(12) United States Patent
Bille et al.

(10) Patent No.: US 10,487,325 B2
(45) Date of Patent: Nov. 26, 2019

(54) GATA-3 INHIBITORS FOR USE IN THE TREATMENT OF TH2-DRIVEN ASTHMA

(71) Applicant: STERNA BIOLOGICALS GMBH & CO. KG, Marburg (DE)

(72) Inventors: Joachim Bille, Reiskirchen (DE); Jonas Renz, Marburg (DE)

(73) Assignee: STERNA BIOLOGICALS GMBH & CO. KG, Marburg (DE)

(*) Notice: Subject to any disclaimer, the term of this patent is extended or adjusted under 35 U.S.C. 154(b) by 0 days.

(21) Appl. No.: 15/574,345

(22) PCT Filed: May 12, 2016

(86) PCT No.: PCT/EP2016/000782
§ 371 (c)(1),
(2) Date: Nov. 15, 2017

(87) PCT Pub. No.: WO2016/184556
PCT Pub. Date: Nov. 24, 2016

(65) Prior Publication Data
US 2019/0062737 A1 Feb. 28, 2019

(30) Foreign Application Priority Data
May 15, 2015 (EP) ..................................... 15001472

(51) Int. Cl.
| C12N 15/113 | (2010.01) |
| A61K 31/711 | (2006.01) |
| A61K 45/06 | (2006.01) |
| A61K 31/7088 | (2006.01) |
| A61K 9/00 | (2006.01) |
| A61P 11/06 | (2006.01) |

(52) U.S. Cl.
CPC .......... *C12N 15/113* (2013.01); *A61K 9/0073* (2013.01); *A61K 31/7088* (2013.01); *A61K 31/711* (2013.01); *A61K 45/06* (2013.01); *A61P 11/06* (2018.01); *C12N 2310/127* (2013.01)

(58) Field of Classification Search
None
See application file for complete search history.

(56) References Cited

U.S. PATENT DOCUMENTS

| 7,355,035 B1 | 4/2008 | Atkins et al. | |
| 2010/0249216 A1* | 9/2010 | Sel | C12N 15/113 514/44 R |

FOREIGN PATENT DOCUMENTS

| WO | WO-2000/09672 A1 | 2/2000 |
| WO | WO-2000/51621 A1 | 9/2000 |
| WO | WO-2001011023 A1 | 2/2001 |
| WO | WO-2002/068637 A2 | 9/2002 |
| WO | WO-2014040891 A2 | 3/2014 |

OTHER PUBLICATIONS

International Search Report and Written Opinion for Application No. PCT/EP2016/000782, dated Aug. 5, 2016.
International Preliminary Report on Patentability for Application No. PCT/EP2016/000782 dated Nov. 30, 2017.
L. Marsh et al., "Anti-inflammatory effects of a human GATA-3-specific DNAzyme in difference mouse models of allergic airway inflammation," *30th Congress of the European Academy of Allergy and Clinical Immunology (EAACI)*, vol. 66, No. 94, 53, p. 25 (2011).
Choladda Vejabhuti Curry, "Differential Blood Count: Reference Range, Interpretation, Collection and Panels," *National Library of Medicine* (2015).
Alesya A. Fokina et al., "DNA enzymes as potential therapeutics: towards clinical application of 10-23 DNAzymes," Expert Opinion on Biological Therapy, vol. 15, No. 5 (2015).
Anonymous, "NCT01743768 on Mar. 7, 2014". Retrieved from the Internet at: <URL:https://clinicaltrials.gov/archive/NCT01743768/2014_03_07 (2015).
Tanja Maria Dicke: "Charakterisierung GATA-3-spezifishcher DNAzyme and Analyse der therapeutischen Wirksamkeit in experimentellen Modellen des allergischen Asthma Bronchiale". Retrieved from the internet at: <URL:https://archiv.ub.uni-marburg.de/diss/z2009/0559/pdf/dtmd.pdf (2008).
Serdar Sel, MD, et al., "Effective prevention and therapy of experimental allergic asthma using a GATA-3-specific DNAzyme," *Journal of Allergy and Clinical Immunology*, vol. 121, No. 4, pp. 910-916 (2008).
Dicke et al., "Gata-3-specific DNAzyme as an Approach for Asthmatherapy," *Journal of Allergy and Clinical Immunology*, vol. 119, No. 1, pp. S1 (2007).
Harald Renz, "Press Release sterna biologicals co-founder Prof. Harald Renz to present key phase IIa results at ATS." Retrieved from the internet at: <URL:http://www.sterna-biologicals.com/images/stories/PDF/pr14may14.pdf (2015).
Fuhst et al., "Toxicity profile of the GATA-3-specific DNAzyme hgd40 after inhalation exposure," *Pulmonary Pharmacology & Therapeutics*, vol. 26, No. 2, pp. 281-289 (2013).
Agnieszka Turowska et al., "Biodistribution of the GATA-3-specific DNAzyme hgd40 after inhalative exposure in mice, rats and dogs," *Toxicology and Applied Pharmacology*, vol. 272, No. 2, pp. 365-372 (2013).

(Continued)

*Primary Examiner* — Tracy Vivlemore
(74) *Attorney, Agent, or Firm* — Marshall, Gerstein & Borun LLP

(57) ABSTRACT

The invention relates to GATA-3 inhibitors for use in the treatment of Th2-driven asthma, in particular to DNAzymes directed at GATA-3 for use in the treatment of a patient suffering from allergic asthma, wherein the patient is characterized by (i) a blood eosinophil count of 3% or more, particularly of 4% or more, more particularly of 5% or more; and/or (ii) blood eosinophil count of $350 \times 10^6$/L or more, particularly of $450 \times 10^6$/L or more; and/or (iii) fractional expiratory nitric oxide of 40 ppb or more.

19 Claims, 17 Drawing Sheets

Specification includes a Sequence Listing.

(56) References Cited

OTHER PUBLICATIONS

Homburg U et al., "Safety and tolerability of a novel inhaled GATA3 mRNA targeting DNAzyme in patients with $T_H2$-driven asthma," *Journal of Allergy and Clinical Immunology*, vol. 136, No. 3, pp. 797-800 (2015).
Caramori G., "Allergen Responses Modified by a GATA3 DNAzyme," *New England Journal of Medicine*, vol. 373, No. 12, pp. 1176-1177 (2015).
Santoro S. W. et al., "A general purpose RNA-cleaving DNA enzyme", *Proc. Natl. Acad. Sci.*, vol. 94, pp. 4262-4266 (1997).
Sun L. Q. et al., "Catalytic Nucleic Acids: From Lab to Applications", The American Society for Pharmacology and Experimental Therapeutics, *Pharmacological Review*, pp. 325-347 (2000).
Imagawa S. et al., "Negative Regulation of the Erythropoietin Gene Expression by the GATA Transcription Factors", *Blood*, vol. 80, No. 4, pp. 1430-1439 (1997).

\* cited by examiner

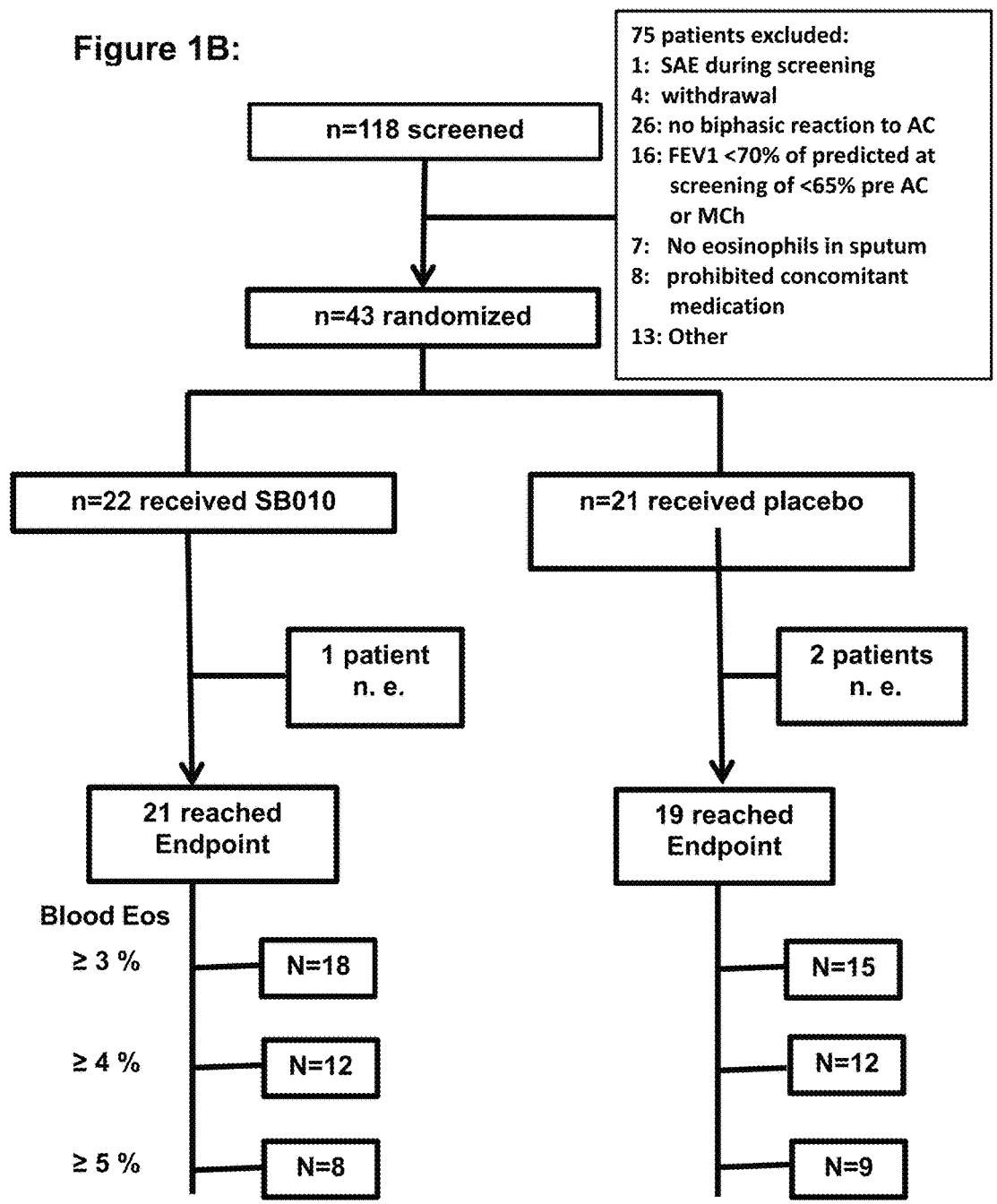

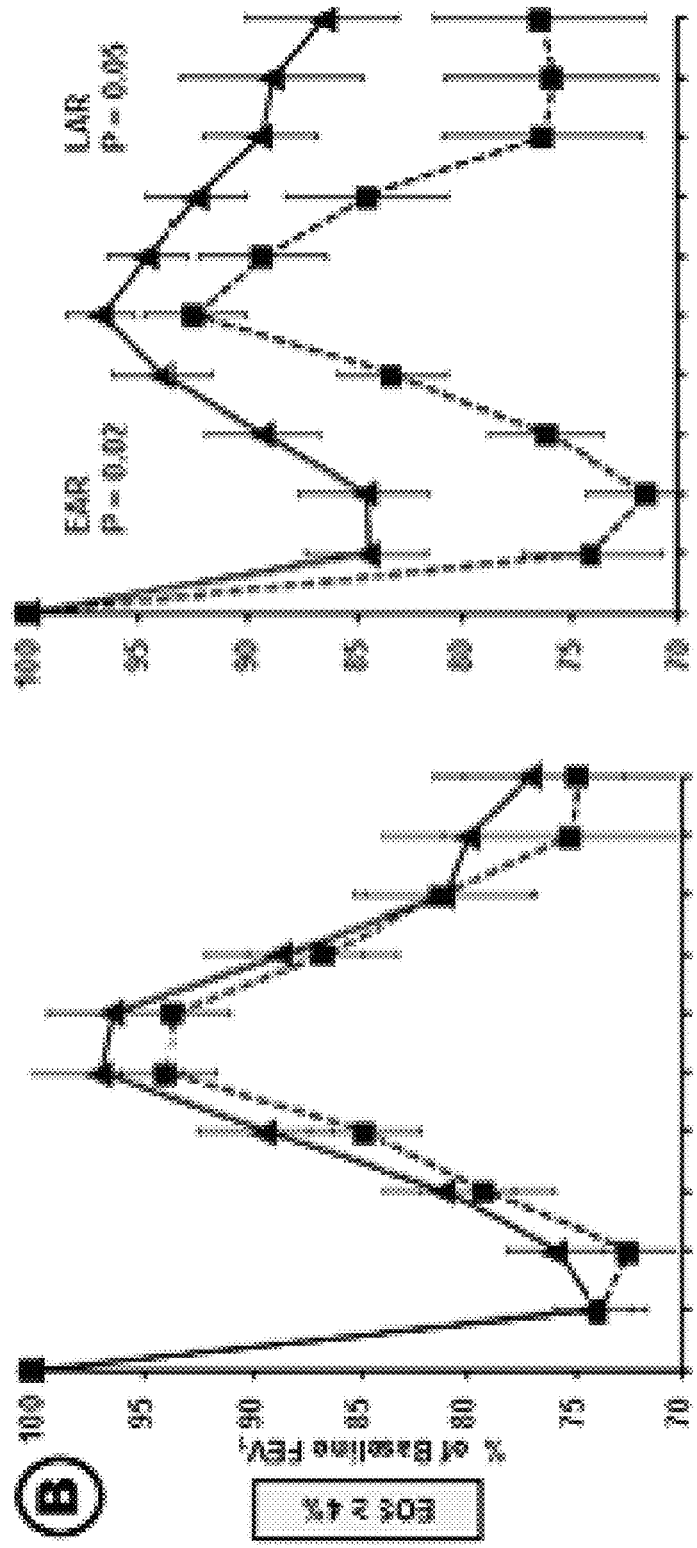
Figure 2A (contd.):

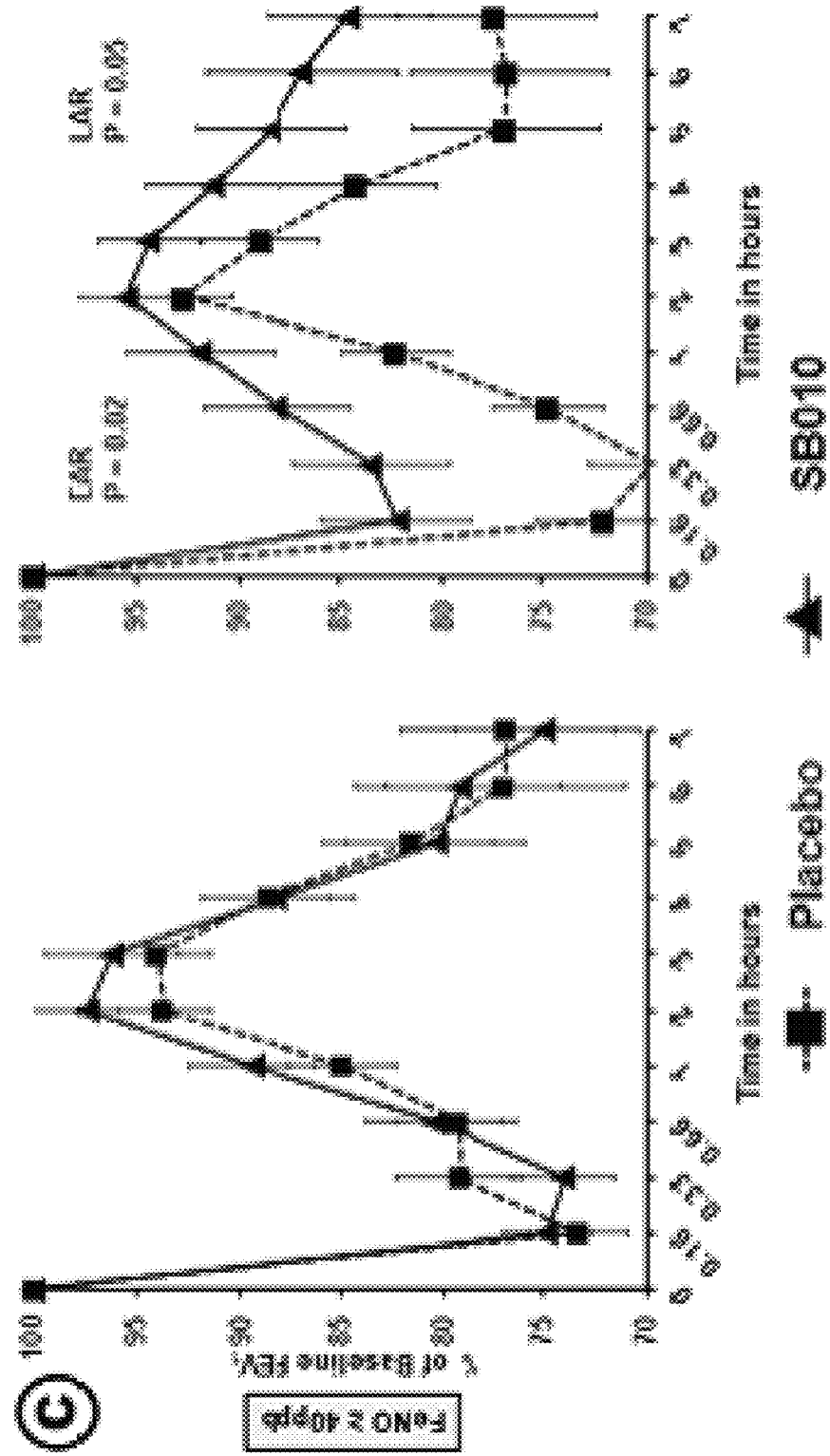
Figure 2A (contd.):

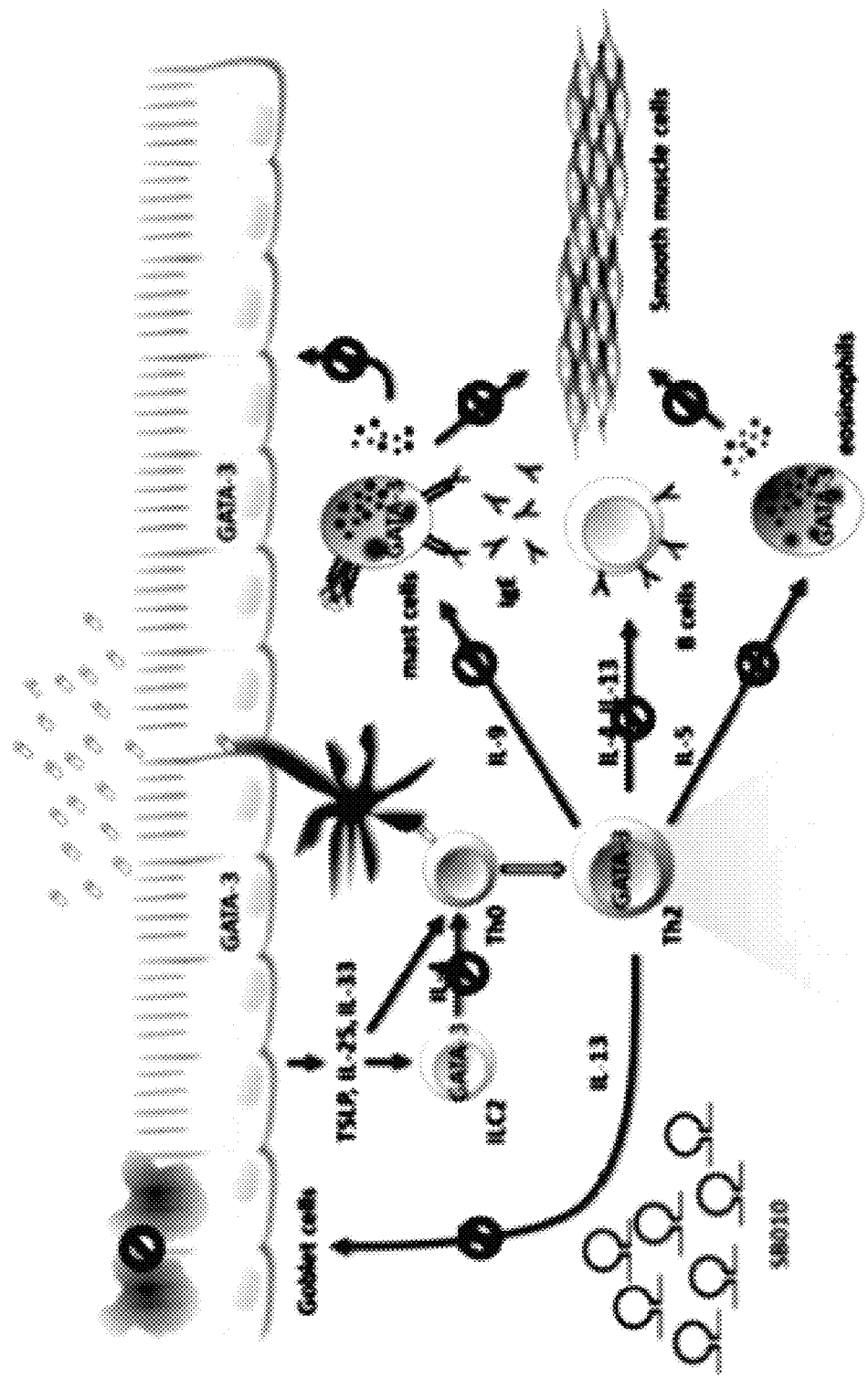
Figure 5 = Figure S1:

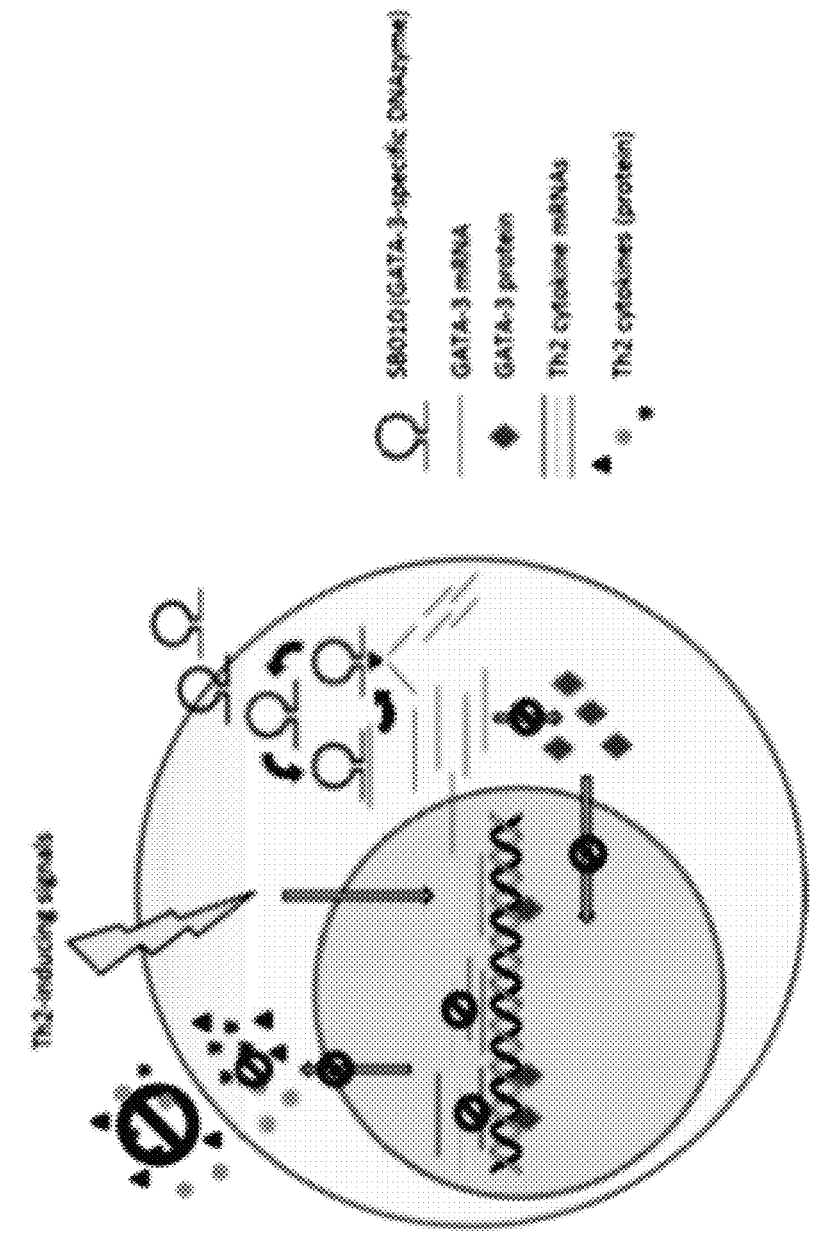
Figure 5 = Figure S1 (contd.):

Figure 6 = Figure S2:
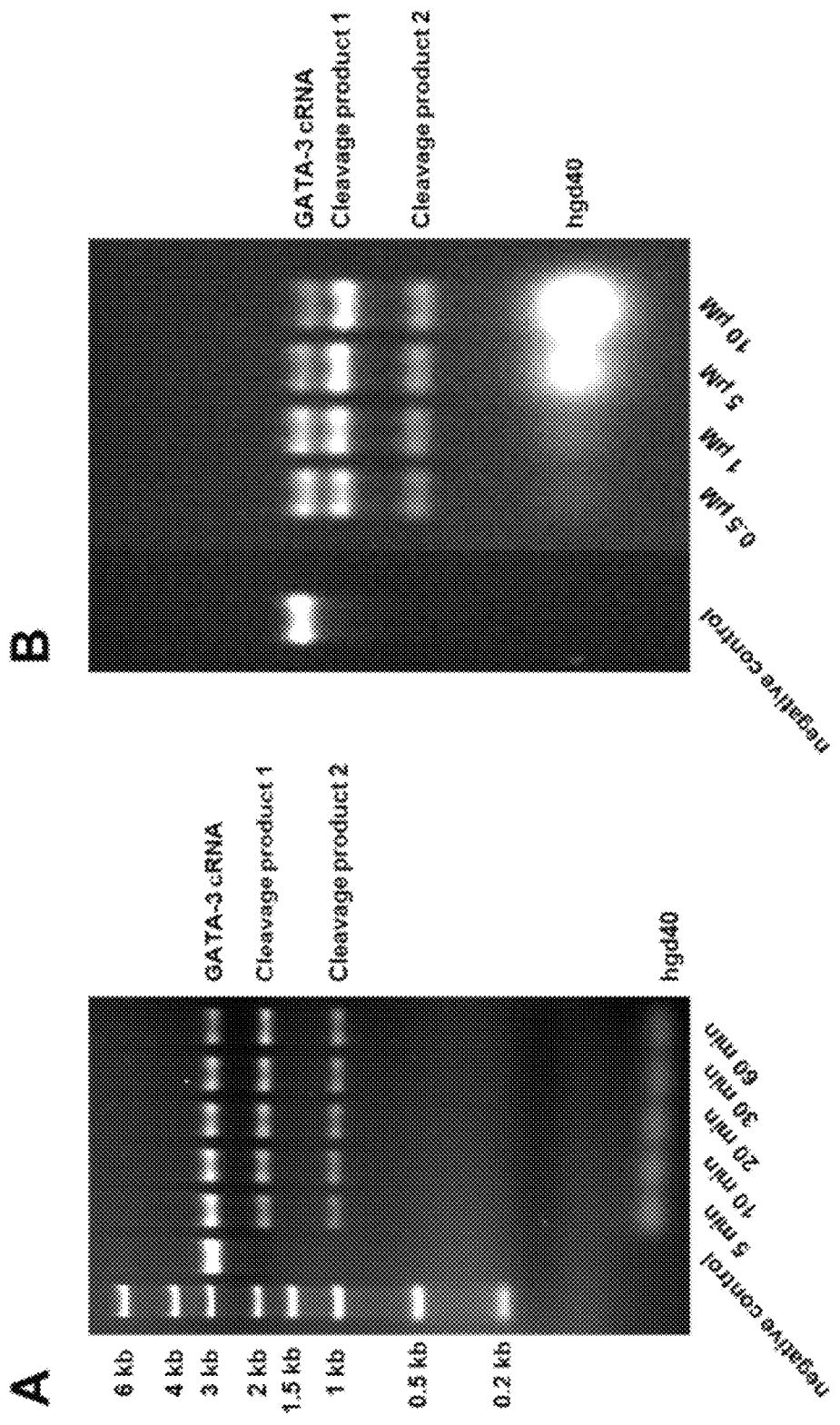

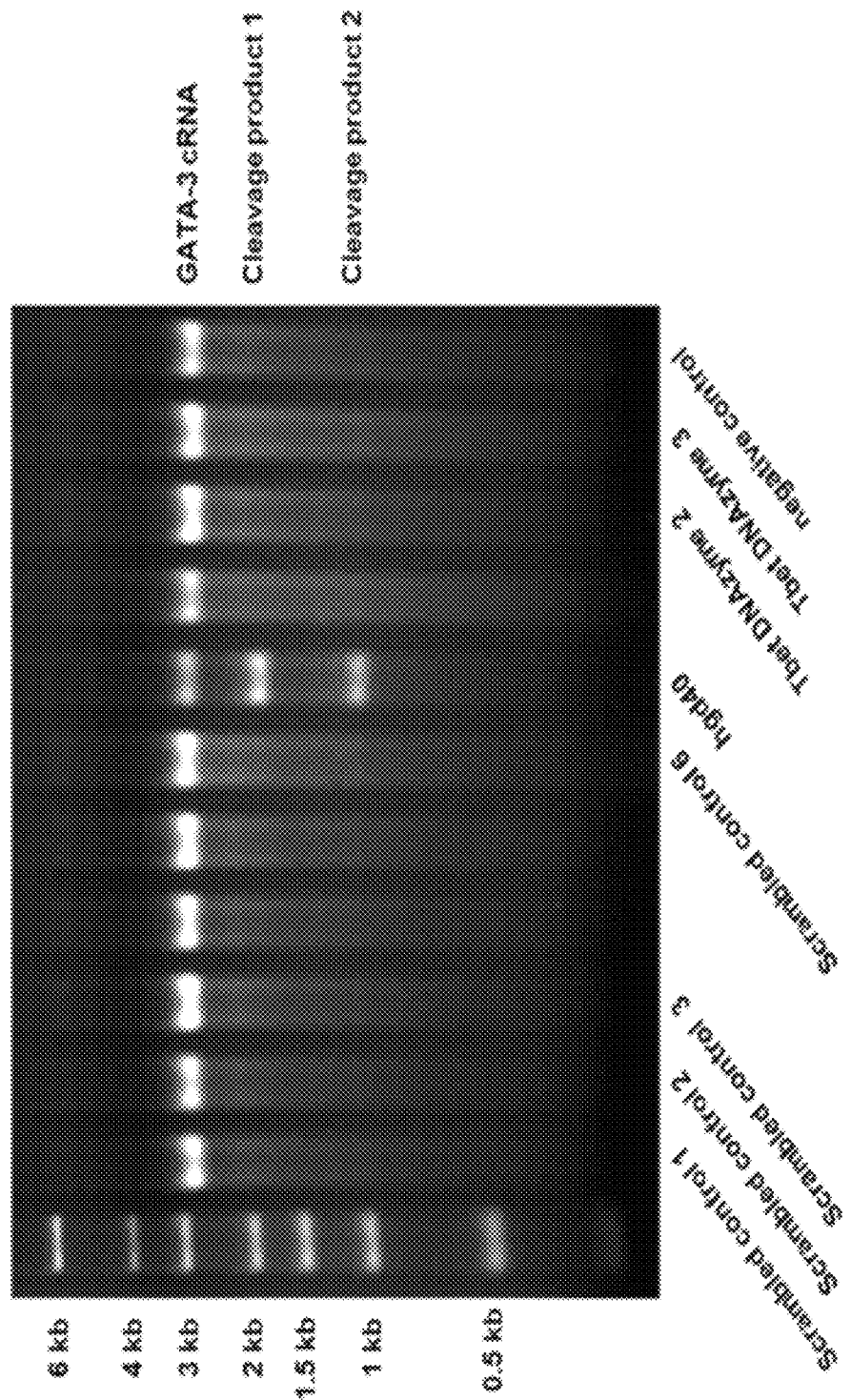
Figure 6 = Figure S2 (contd.):

Figure 7 = Figure S3:
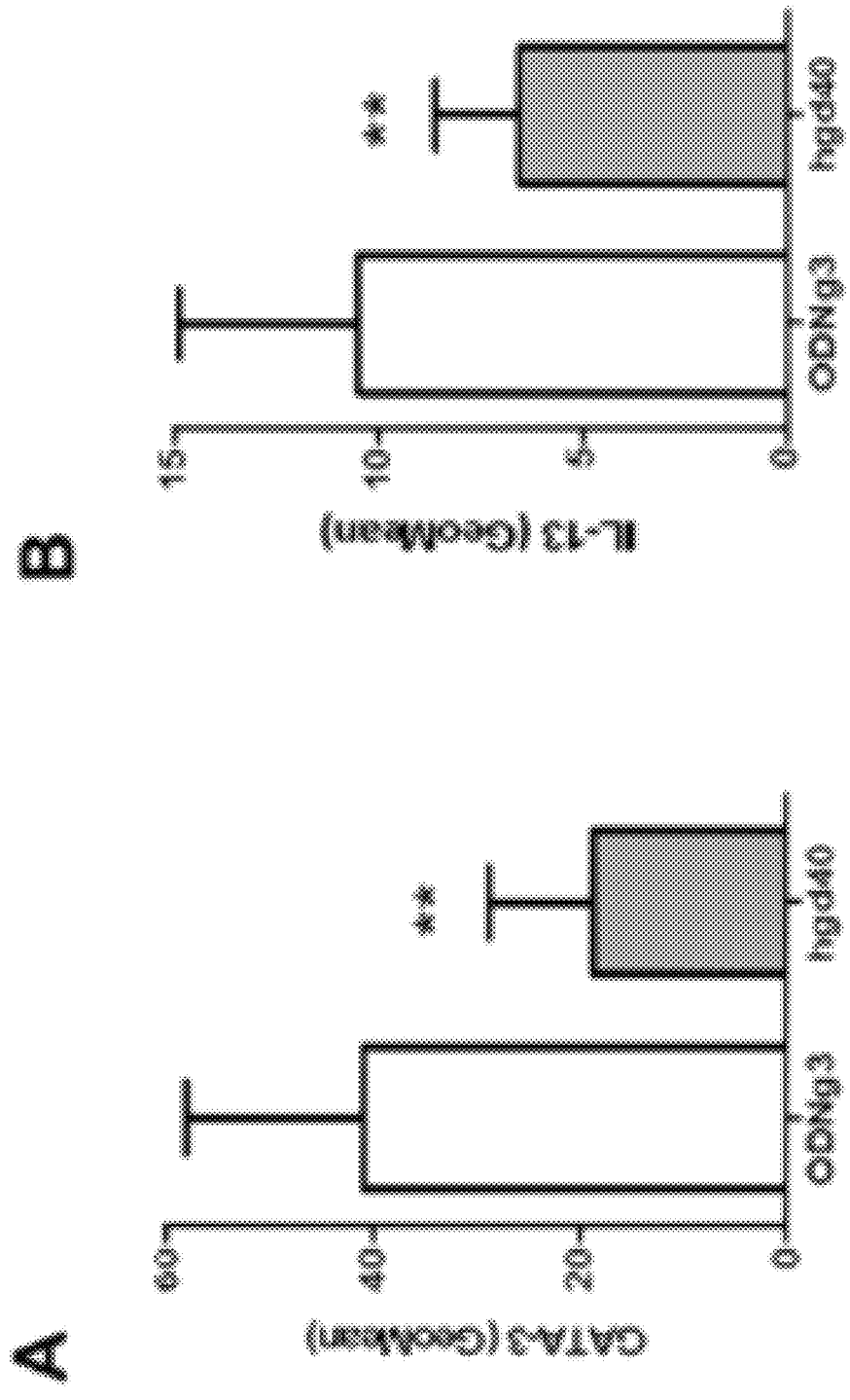

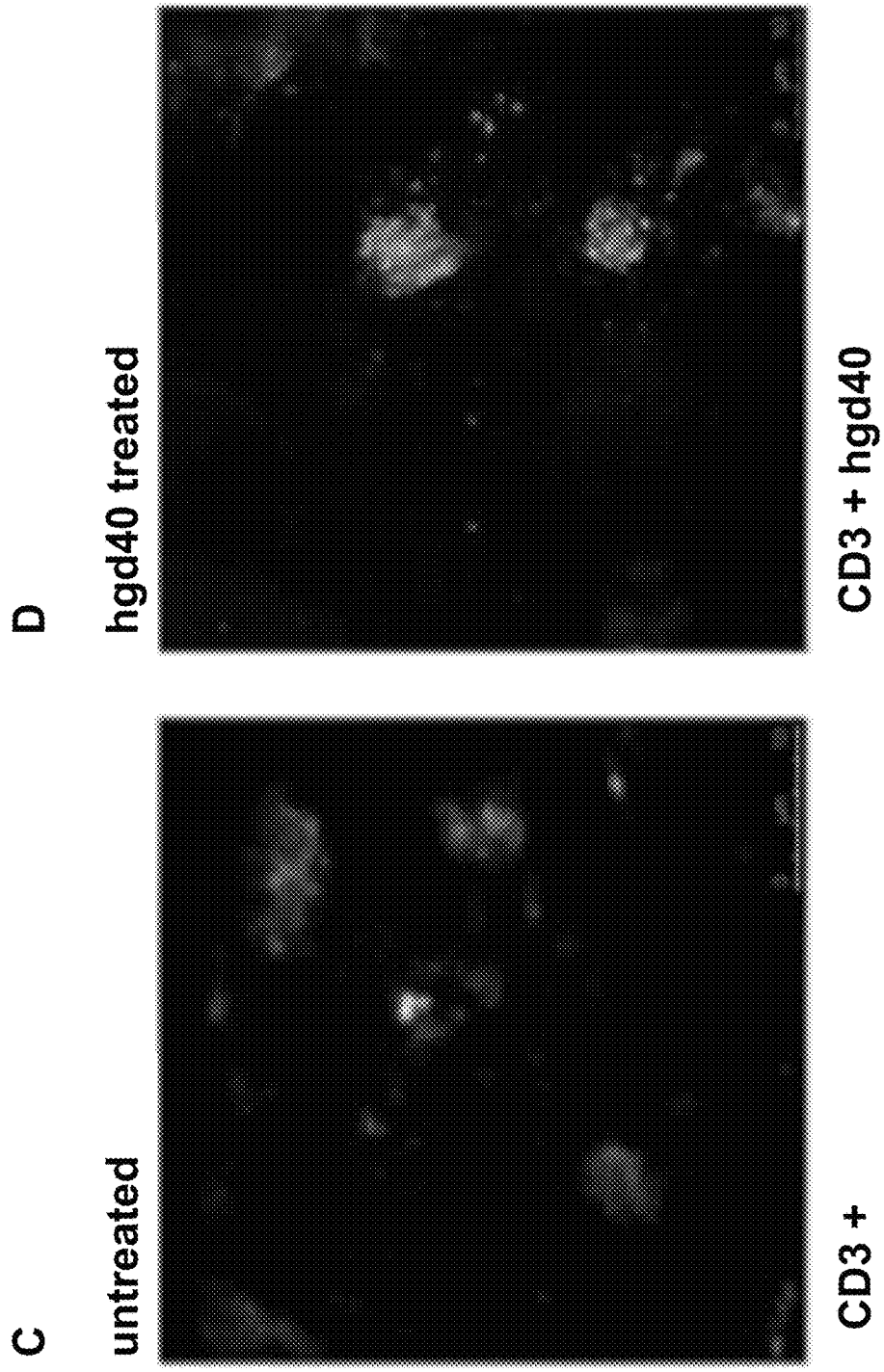
Figure 7 = Figure S3 (contd.):

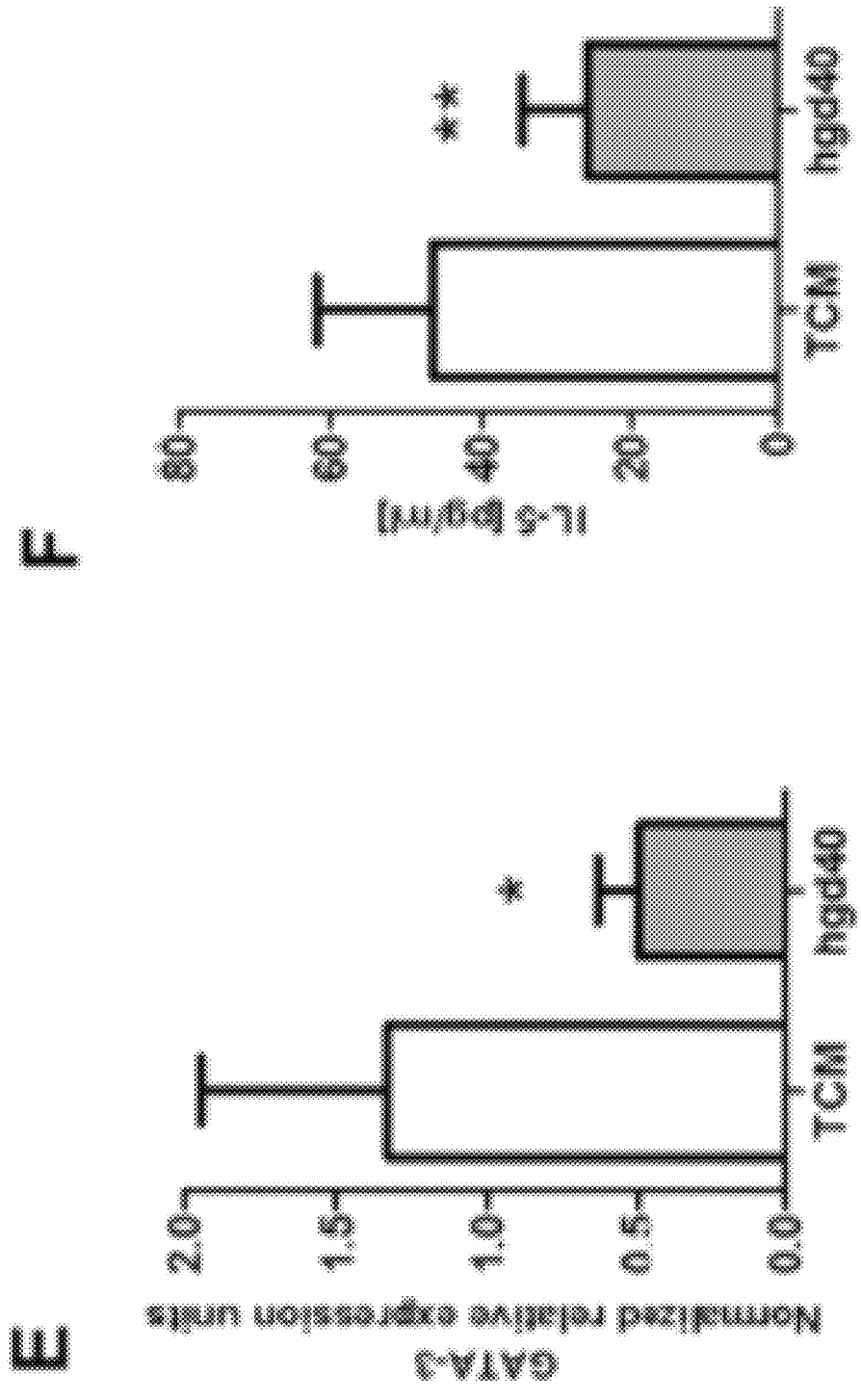
Figure 7 = Figure S3 (contd.):

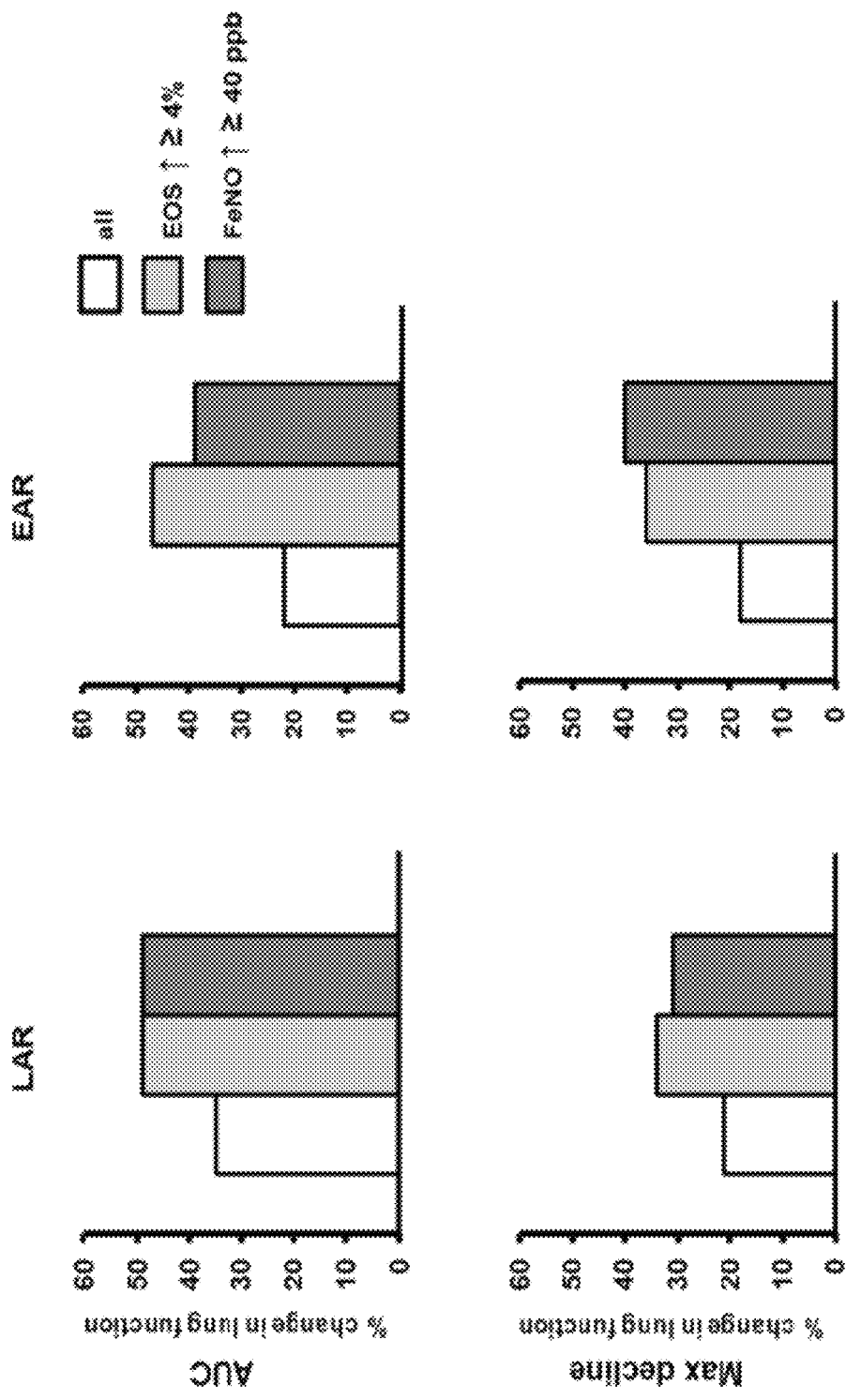
Figure 8 = Figure S4:

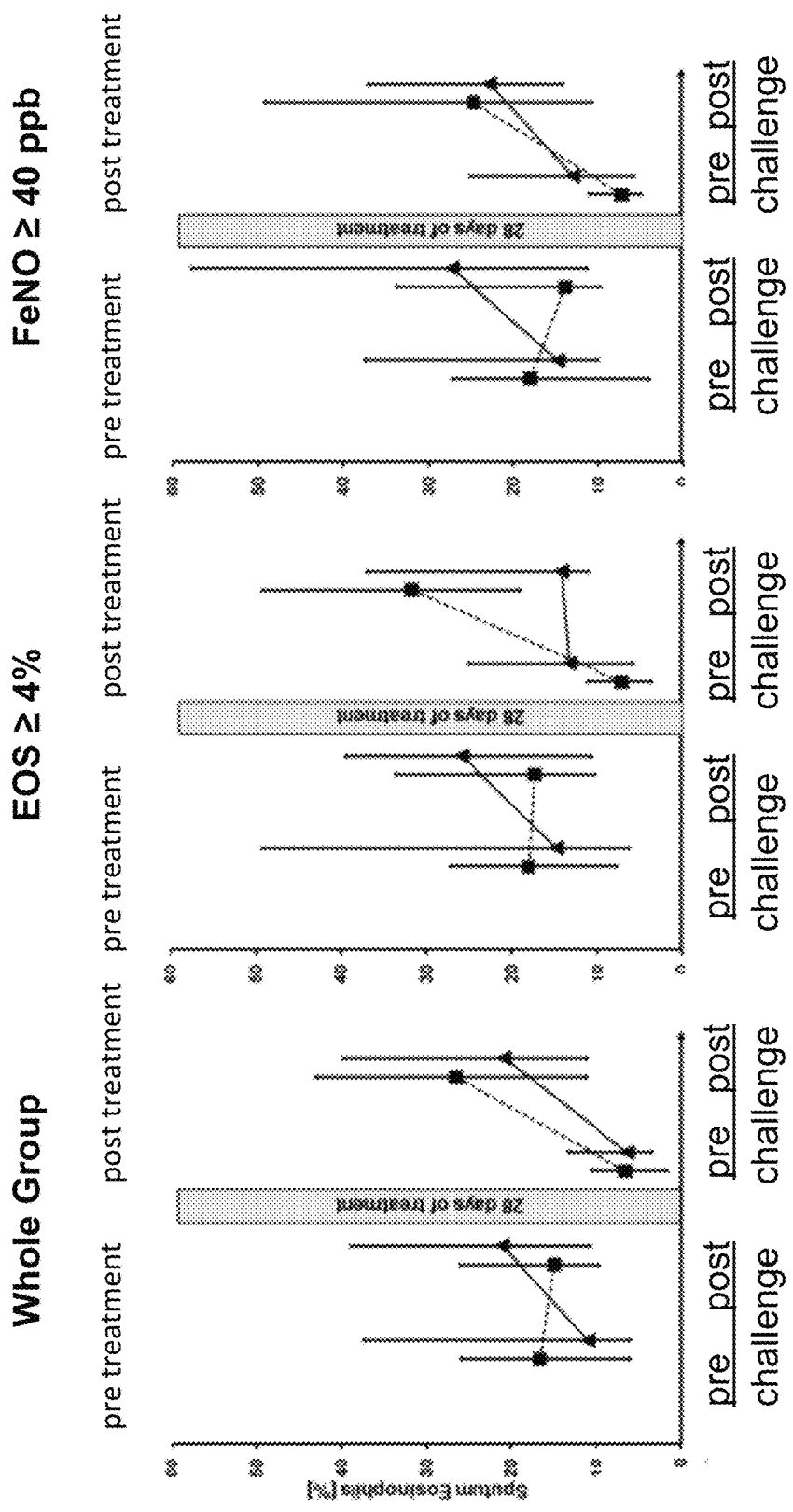
Figure 9 = Figure S5:

GATA-3 INHIBITORS FOR USE IN THE TREATMENT OF TH2-DRIVEN ASTHMA

INCORPORATION BY REFERENCE OF MATERIAL SUBMITTED ELECTRONICALLY

This application contains, as a separate part of disclosure, a sequence listing in computer-readable form (filename: 52456_Seqlisting; Size: 1,075 bytes; created Feb. 13, 2019) which is incorporated by reference in its entirety.

FIELD OF THE INVENTION

The invention relates to GATA-3 inhibitors for use in the treatment of Th2-driven asthma, in particular to DNAzymes directed at GATA-3 for use in the treatment of a patient suffering from allergic asthma, wherein the patient is characterized by (i) a blood eosinophil count of 3% or more, particularly of 4% or more, more particularly of 5% or more; and/or (ii) blood eosinophil count of $350 \times 10^6$/L or more, particularly of $450 \times 10^6$/L or more; and/or (iii) fractional expiratory nitric oxide of 40 ppb or more.

BACKGROUND OF THE INVENTION

Chronic inflammations constitute an increasing medical problem area of high socio-economic significance. This includes in particular the following groups of illnesses: autoimmune diseases and diseases from the area of rheumatic diseases (manifestations among others on the skin, lungs, kidneys, vascular system, nervous system, connective tissue, locomotor system, endocrine system), immediate-type allergic reactions and asthma, chronic obstructive lung diseases (COPD), arteriosclerosis, psoriasis and contact eczema and chronic rejection reactions after organ and bone marrow transplants. Many of these diseases are showing a rising prevalence in the last decades not only in industrial nations, but sometimes around the world. For example, in Europe, North America, Japan and Australia more than 20% of the population suffers from allergic diseases and asthma. Chronic obstructive lung diseases are currently the fifth most frequent cause of death throughout the world and according to calculations of the WHO they will represent the third most frequent cause of death in the year 2020. Arteriosclerosis with the secondary diseases of cardiac infarction, stroke and peripheral arterial disease leads the world in morbidity and mortality statistics. Together with neurodermatitis, psoriasis and contact eczema are in general the most frequent chronic inflammatory diseases of the skin.

Asthma is a common chronic inflammatory disease of the airways, comprising variable airway obstruction, mucus hyper-secretion, airway inflammation and increased airway hyper-responsiveness. Dysregulation of innate and adaptive immune responses is considered to play a central role in the development of the disease. A high degree of inter-individual heterogeneity has been identified among different patient populations leading to the definition of several clinical phenotypes and pathophysiological endotypes.[1] The best studied pathophysiological asthma condition is the T-helper (TH)-2 driven (allergic) response[2,3], which is also termed the "TH2 molecular endotype"[4,5].

Approximately half of patients with asthma, regardless of disease severity, exhibit this TH2 endotype, which is characterized by a predominant activation of TH2 cells producing cytokines such as IL-4, IL-5, and IL-13. The expression and production of all these TH2 cytokines is critically controlled by the zinc finger transcription factor GATA-3, which is essential for TH2 cell differentiation and activation and considered the master transcription factor of the type 2 (TH2) pathway of immune activation[6]. GATA-3 is primarily responsible for the differentiation of naïve CD4⁺ T cells to TH2 cells. In the process, the TH2 cell differentiation is primarily controlled by two signal transmission pathways, the T cell receptor (TZR) and the IL-4 receptor pathway: Signals forwarded from TZR activate the TH2 cell-specific transcription factors cMaf and GATA-3 as well as also the transcription factors NFAT and AP-1. The activation of the IL-4 receptor results in the binding of STAT6 on the cytoplasmic domain of the IL-4 receptor, where it is phosphorylated by Jak1 and Jak3 kinases. The phosphorylation for its part results in the dimerization and translocation of STAT6 to the nucleus, where STAT6 activates the transcription of GATA-3 and other genes. GATA-3 is a zinc finger transcription factor which is expressed exclusively in mature TH2 cells, not in TH1 cells. GATA-3 overexpression has been observed in bronchoalveolar lavage samples and lung biopsies from patients with severe asthma despite optimal therapy according to the GINA guidelines[7]. This immune network is therefore a promising therapeutic target. In addition to the already approved anti-IgE monoclonal antibodies, several new therapeutics targeting individual components downstream of the transcription factor GATA-3 are in development[8].

An alternative approach directly targets the strategic transcription factor GATA-3 to interfere with all downstream molecules/cytokines simultaneously. GATA-3 expression has been analyzed in order to determine the molecular phenotype of patients suffering from chronic inflammatory diseases and to stratify patients in "TH2 high" and "TH2 low" subgroups, and it was suggested to treat "TH2 high" patients with GATA-3 specific inactivators (WO 2014/040891). Since GATA-3 is only expressed intracellularly, nucleic acid-based inactivators of GATA-3, such as GATA-3-specific DNAzymes, with in vivo cell-penetrating capabilities have been developed (WO 2005/033314).

In chronic inflammatory disorders, such as in allergic asthma, the problem of identifying an appropriate treatment scheme is more complex though. It is known that in allergic reactions, the number of eosinophils is increased, resulting in eosinophilia in certain patients. Eosinophils, however, are known to express GATA-3 as well (Zon et al., Blood 81 (1993) 3234-3241), since the expression of GATA-3 is not restricted to T cells, and expression of GATA-3 was also able to be confirmed in basophils, mast cells and epithelial cells. GATA-3 plays a central role in the immunopathogenesis of chronic inflammatory diseases, in particular of allergic asthma. It was shown that an acute sensitization and challenge with an allergen results in a high degree of eosinophil accumulation in the airways with minimal recruitment of lymphocytes (Paul Justice et al., Am J Physiol Lung Cell Mol Physiol 282 (2002) L302-L309), and that allergen challenge induces expression of GATA-3 and GATA-3-responsive genes in pulmonary eosinophils. In summary, it was postulated that eosinophils might provide positive feedback for the inflammatory response. In contrast, it had been shown that in chronic allergic airway inflammation, such as in allergic asthma, 60-90% of the GATA-3-positive cells in human lung tissue were CD3-positive T cells, and only less than 15% of the cells were identified as eosinophils (Nakamura et al., J Allergy Clin Immunol 103 (1999) 215-222). It was therefore concluded that in human asthma, eosinophil expression of GATA-3-responsive genes was likely not the primary source of proinflammatory cytokines leading to airway inflammation, but might just provide a redundant source of TH2 cytokines to support the chronic inflammatory process (Paul Justice et al., loc. cit.).

Thus, while GATA-3 in TH2 cells appears to be an attractive target for therapeutic intervention in the case of allergic disorders such as allergic asthma, it was completely unknown, what impact, if any, the simultaneous presence of eosinophils, which express GATA-3 as well, might have on the success of such a treatment approach. It was furthermore not predictable at all, whether it would be possible to identify certain patient populations that particularly benefit from such an approach.

Thus, there is still a large unmet need to develop novel and efficient therapies for patients with allergic asthma. The solution presented in this application, which is based on the identification of certain patient populations that particularly benefit from the administration of certain GATA-3 inhibitors, was not knows so far and could not have been expected by anyone of ordinary skill in the art.

SUMMARY OF THE INVENTION

The invention relates to GATA-3 inhibitors for use in the treatment of Th2-driven asthma, in particular to DNAzymes directed at GATA-3 for use in the treatment of certain subpopulations of patients suffering from allergic asthma.

Thus in a first aspect, the present invention relates to a nucleic acid-based inactivator of GATA-3, particularly a DNAzyme directed at GATA-3, for use in the treatment of a patient suffering from allergic asthma, wherein the patient is characterized by (i) a blood eosinophil count of 3% or more, particularly of 4% or more, more particularly of 5% or more; and/or (ii) blood eosinophil count of $350 \times 10^6$/L or more, particularly of $450 \times 10^6$/L or more; and/or (iii) fractional expiratory nitric oxide of 40 ppb or more.

In a second aspect, the present invention relates to a method of treating a patient suffering from Th2-driven asthma, in particular allergic asthma, wherein the patient is characterized by (i) a blood eosinophil count of 3% or more, particularly of 4% or 5% or more, respectively; and/or (ii) blood eosinophil count of $350 \times 10^6$/L or more, particularly of $450 \times 10^6$/L or more; and/or (iii) fractional expiratory nitric oxide of 40 ppb or more, wherein said method comprises the step of administering a nucleic acid-based inactivator of GATA-3, particularly a DNAzyme directed at GATA-3, to said patient.

BRIEF DESCRIPTION OF THE DRAWINGS

FIG. 2 shows the changes in lung function following allergen challenge before and after 4 weeks of treatment.

FIG. 5 (=Figure S1 of the Supplementary Appendix) shows the central role of Th2 cells and GATA-3 in the pathogenesis of allergic asthma and mode-of-action of SB010, as discussed in the Supplementary Appendix.

FIG. 6 (=Figure S2 of the Supplementary Appendix) shows the mRNA cleavage activity and the GATA-3 DNAzyme as discussed in the Supplementary Appendix. In vitro cleavage activity of the GATA-specific DNAzyme hgd40 for GATA-3 copy (c)RNA. In vitro transcribed full open reading frame cRNA was incubated for different time intervals (kinetics—A) or with increasing doses (dose dependency—B) of hgd40 and resulting cleavage products were separated and ethidium bromide-stained on agarose gels. Similarly, GATA-3 cRNA was incubated with unspecific DNAzymes either with scrambled binding domains but intact catalytic sequence (scrambled DNAzymes 1-6) or DNAzymes directed against a different transcription factor sequence (T box transcription factor Tbet, Tbet DNAzymes 1-3) to demonstrate sequence specificity of the DNAzyme approach (C).

FIG. 7 (=Figure S3 of the Supplementary Appendix) shows the bioactivity of hgd40—the active component of SB010 and the effects of hgd40 treatment on human primary T cells and nasal tissue explants. A—Reduction of GATA-3 protein expression by hgd40 transfection of human polarized Th2 cells. B—Reduction of IL-13 secretion by hgd40 transfection of human polarized Th2 cells. Data from Figure S2A and S2B represent intracellular staining of FAM-positive transfected cells and are presented as mean+SEM for n=8-10 per group. C and D—Uptake of fluorescently labeled hgd40 (red color) by CD3+ T cells (green color) present in human nasal polyp tissue explants obtained from patients suffering from chronic rhinosinusitis with nasal polyps (CRSwNP). Results were obtained by confocal laser scanning microscopy and presented as overlay of both colors for untreated (Figure C) and hgd40 treated cells (Figure D). E—Expression of GATA-3 mRNA in human nasal polyp tissue explants obtained from patients suffering from CRSwNP in an ex vivo tissue assay. Data are expressed as normalized relative expression units and presented as mean+SEM for n=6 per group. F—Release of IL-5 protein from human nasal polyps in an ex vivo tissue assay. Data are presented as mean+SEM for n=16 per group. Significance was calculated by students' t test using GraphPad Prism 5; (*) P<0.05; (**) P<0.01. For technical details see Supplementary Appendix, Material and Methods.

FIG. 8 (=Figure S4 of the Supplementary Appendix) shows mean treatment difference in entire ITT population and pre-specified subgroups. This is a visualization of the group differences reflecting the delta of relative changes between SB010 treatment and placebo group. Values for the entire study population are shown in Table S2, values for the pre-specified subgroup of patients with blood eosinophils ≥4% are depicted in Table S3a, and values for the pre-specified subgroup of patients with FeNO ≥40 ppb are found in Table S3B. Top: percent change in lung function between pre- and post-treatment is expressed as area under the curve (AUC). Bottom: expressed are percent changes in lung function as maximal decline in $FEV_1$. EAR: early phase asthmatic response; LAR: late phase asthmatic response.

FIG. 9 (=Figure S5 of the Supplementary Appendix) shows the effect of SB010 and placebo treatment on sputum eosinophils (in percent). Measurements were performed in induced sputum samples, before and after allergen inhalation as described in Material and Methods. Allergen inhalation was carried out before and after 28 days of treatment with SB010 (▲) and placebo (■). Shown are median values and 25th and 75th percentile ranges for each time point and treatment group. Left panel: the group as a whole; middle panel: pre-specified subgroup, blood eosinophils ≥4%; right panel: pre-specified subgroup, FeNO ≥40 ppb. In the group as a whole the absolute change in post challenge percent eosinophils shows a non-significant trend (P=0.06) between the treatment groups, which became significant in the eosinophil subgroup (P=0.009) and in the FeNO subgroup (P=0.02). This decrease in percent sputum eosinophils was not due to an increased influx of neutrophils, as depicted in Table S8 in the Supplementary Appendix.

DETAILED DESCRIPTION OF THE INVENTION

Figure 1A:
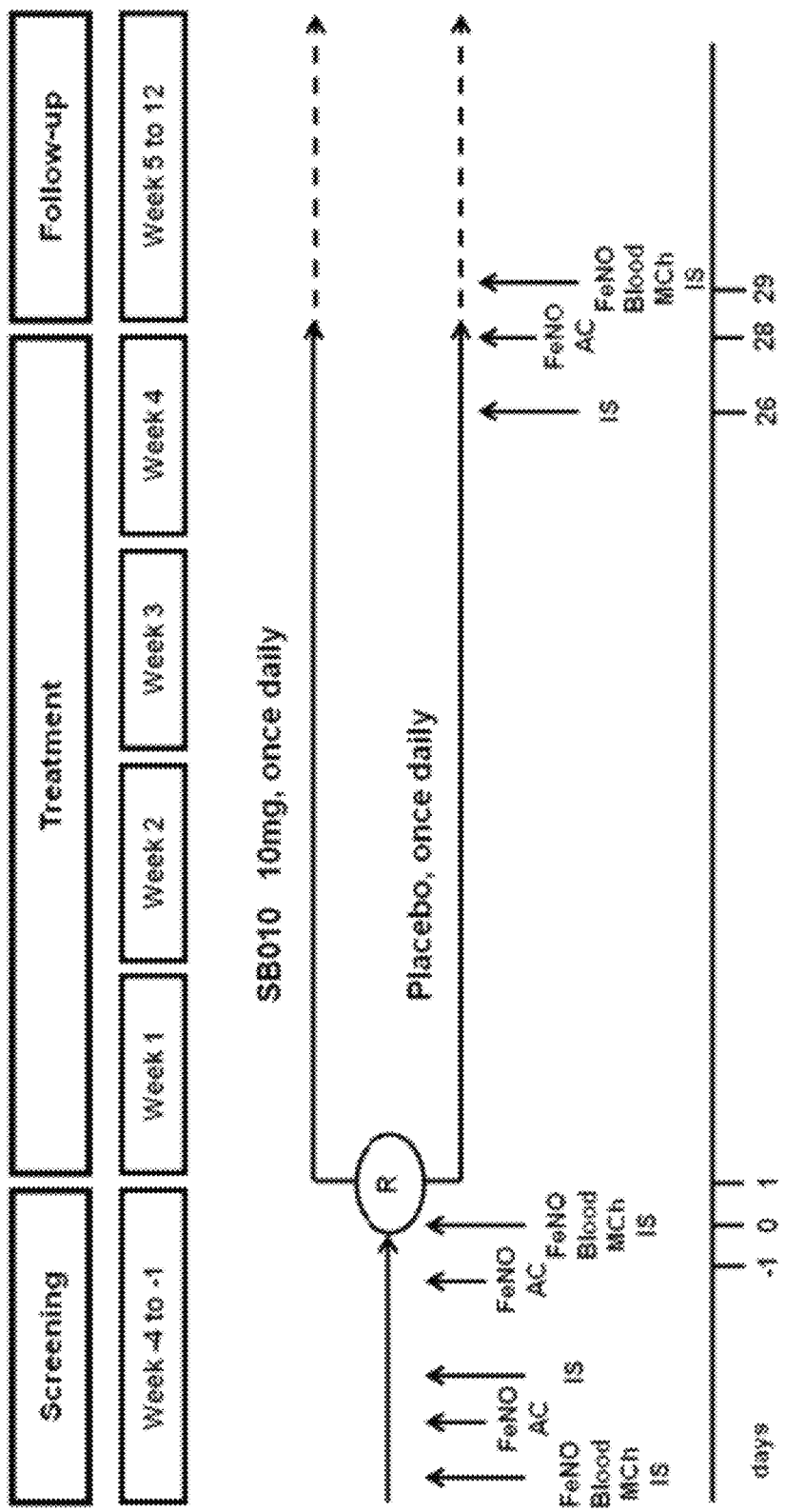
FIG. 1 shows study design and flowchart. Panel A shows an overview of study design and main study procedures. Panel B summarizes the number of patients enrolled and included in the analyses. Twenty-one patients in the SB010 group completed all study assessments, one patient was not eligible for evaluation because of administration of a different allergen dose in the pre- and post-treatment allergen challenges. In the placebo group two patients were not eligible for evaluation (1 patient required SABA during the allergen challenge; 1 patient was administered a different allergen dose in the pre- and post-treatment allergen challenges). Therefore, 21 evaluable patients in the SB010 group and 19 evaluable patients in the placebo group completed the study"*": In the placebo group LAR data is missing for 1 patient since serial spirometry was unintentionally stopped 4 hours after allergen provocation.

The invention relates to nucleic acid-based inactivators, particularly DNAzymes, for use in the treatment of Th2-driven asthma, in particular to nucleic acid-based inactivators, particularly DNAzymes, directed at GATA-3 for use in the treatment of certain patient subpopulations.

Thus in a first aspect, the present invention relates to a nucleic acid-based inactivator of GATA-3, particularly a DNAzyme directed at GATA-3, for use in the treatment of a patient suffering from allergic asthma, wherein the patient is characterized by (i) a blood eosinophil count of 3% or more, particularly of 4% or more, more particularly of 5% or more; and/or (ii) blood eosinophil count of $350×10^6$/L or more, particularly of $450×10^6$/L or more; and/or (iii) fractional expiratory nitric oxide of 40 ppb or more.

In a second aspect, the present invention relates to a method of treating a patient suffering from Th2-driven asthma, in particular allergic asthma, wherein the patient is characterized by (i) a blood eosinophil count of 3% or more, particularly of 4% or 5% or more, respectively; and/or (ii) blood eosinophil count of $350×10^6$/L or more, particularly of $450×10^6$/L or more; and/or (iii) fractional expiratory nitric oxide of 40 ppb or more, wherein said method comprises the step of administering a nucleic acid-based inactivator of GATA-3, particularly a DNAzyme directed at GATA-3, to said patient.

In the context of the present invention, the term "nucleic acid-based inactivator" refers to a nucleic acid-based substances that is at least partially complementary to a target gene sequence, and which inactivates the target gene activity, e.g. by blocking reduplication, transcriptions or translation, or by cleaving the target sequence. A nucleic acid-based inactivator may consist of ribonucleotides, desoxyribonucleotides, non-naturally occurring nucleotides and mixtures thereof, and may be a single-stranded sequence, a double-stranded sequence or a mixture thereof. Nucleic-acid based inactivators in accordance with the present invention include siRNA molecules, shRNA molecules, and DNAzymes.

In the context of the present invention, the term "DNAzymes" refers to catalytically active single-stranded, synthetic DNA molecules, which do not occur in nature. DNAzymes of the 10-23 family represent a new class of antisense molecules, which were developed in the 1990s, but have only recently been finding clinical applications[9].

In the context of the present invention, the term "10-23 family" refers to a general DNAzyme model (Sontoro & Joyce, Proc. Natl. Acad. Sci. U.S.A., 94 (1997) 4262-4266). DNAzymes of the 10-23 model—also referred to as "10-23 DNAzymes" have a catalytic domain of 15 desoxyribonucleotides, which are flanked by two substrate binding domains (see WO 2005/033314). Potential advantages of DNAzymes include relatively high stability and no reliance on intracellular enzymes.

In a particular embodiment, the catalytic domain has the sequence ggctagctacaacga (SEQ ID No.: 1). The length of the substrate binding domains is variable: they are either of equal or of different length. In particular embodiments, the substrate binding domains consists of between 6 and 14 nucleotides, more particularly in each case of at least nine nucleotides. Such DNAzymes comprise the general sequence nnnnnnnnnggctagctacaacgannnnnnnnn (SEQ ID NO 2). In particular embodiments of the present invention, the substrate binding domains bind the mRNA coding for the protein GATA-3.

The specified central catalytic domain ggctagctacaacga (SEQ ID No: 1) is only a particular embodiment. A person skilled in the art is aware of the fact that "10-23 DNAzymes" can be obtained with comparable biological activity with a modified catalytic domain.

In one particular embodiment, the substrate binding domains are completely complementary to the regions that flank the cleaving site. However, in order to bind the target RNA and to cleave it, the DNAzyme does not necessarily have to be completely complementary. DNAzymes of the 10-23 type cleave the target mRNA on purine-pyrimidine sequences. Within the scope of the present invention the DNAzymes preferably comprise the in vivo active DNAzymes against GATA-3 in accordance with WO 2005/033314, whose content is herewith incorporated by reference to the extent possible under any applicable patent law.

In particular embodiments of the present invention, the patient has a blood eosinophil count of 4% or more.

In particular embodiments, the patient has a blood eosinophil count of 5% or more.

In particular embodiments of the present invention, the patient has a blood eosinophil count of $350 \times 10^6$/L or more.

In particular embodiments, the patient has a blood eosinophil count of $450 \times 10^6$/L or more.

In particular embodiments of the present invention, the blood eosinophil count is determined by (i) conventional automated differential blood counting (e.g. using Coulter Technology or Sysmex Technology or other technologies), or (ii). manual microscopic cell differentiation using conventional blood smears.

In particular embodiments of the present invention, the patient has fractional expiratory nitric oxide of 40 ppb or more.

In particular embodiments of the present invention, the fractional expiratory nitric oxide is determined using the hand-held NIOX MINO® device.

In particular embodiments of the present invention, the DNAzyme directed at GATA-3 is selected from the sequences hgd1 to hgd70 of WO 2005/033314 (see FIG. 3 of WO 2005/033314), particularly selected from the sequences hgd11, hgd13, hgd17 and hgd40, more particularly sequence hgd40 (5'-GTGGATGGAggctagctacaacgaGTCTTGGAG; SEQ ID NO: 3).

In the context of the present invention, the term "hgd40" refers to a DNAzyme directed at GATA-3, which consists of 34 bases with the sequence 5'-GTGGATGGAggctagctacaacgaGTCTTGGAG (SEQ ID No.: 3). The nine bases at both the 3' and 5' region form two binding domains, which highly specifically bind to the target mRNA of GATA-3. The central core of the molecule represents the catalytic domain which accounts for cleavage of the target following binding of hgd40 to the GATA-3 mRNA[10] (see FIGS. 5 and 6). The drug substance hgd40 is characterized by high bioactivity and bioavailability at the site of drug delivery by inhalation.[12]

In particular embodiments of the present invention, the hgd40 is comprised in a formulation that can be administered to a patient either orally, rectally, parenterally, intravenously, intramuscularly, subcutaneously, intracisternally, intravaginally, intraperitoneally, intrathecally, intravascularly, locally (powder, ointment or drops) or in the form of a spray or inhalant. The active component is mixed under sterile conditions with a physiologically acceptable excipient and possible preservatives, buffers or propellants, depending on requirements.

In particular embodiments of the present invention, the hgd40 is comprised in a formulation for inhalation.

In particular embodiments of the present invention, said hgd40 is dissolved in PBS.

The type of dosage and the dosage scheme will be determined by the attending physician in accordance with the clinical factors. A person skilled in the art is aware of the fact that the type of dosage and dosage scheme is dependent on different factors such as e.g. body size, weight, body surface, age, sex or the general health of the patient, but also depends on the agent to be administered, the duration and type of administration and on other medicaments that may be administered in parallel. In the process, according to an especially advantageous embodiment, the quantity of the active ingredient of the medicament can be adapted to the measured expression level. Thus, in the case of placement in the subgroup "Th2 high" and an established very high GATA-3 gene expression an increase dose of the active ingredient, in particular a DNAzyme specific for GATA-3 specific can be administered. Correspondingly, in the case of placement in the subgroup "Th1 high" and an established very high Tbet gene expression an increased dose of the active ingredient, in particular of a DNAzyme specific for Tbet can be administered.

In particular embodiments of the present invention, the dosage consists of between 5 and 50 mg hgd40, particularly between 5 and 20 mg hgd40, particularly 10 mg of hgd40. In particular embodiments, the dosage is dissolved in 2 ml PBS. In particular embodiments these dosages are the daily dosage amounts.

In particular embodiments of the present invention, said nucleic acid-based inactivator of GATA-3 is administered once daily, two times daily or three times daily, particularly once daily.

In particular embodiments of the present invention, said DNAzyme directed at GATA-3 is administered once daily for 28 consecutive days in continuous therapy, in particular maintenance therapy.

In particular embodiments of the present invention, said nucleic acid-based inactivator of GATA-3 is used as add-on therapy to one or more inhaled or oral therapeutics for the treatment of asthma selected from the list of: corticosteroids, long-acting beta agonists (LABAs), long acting muscarinic antagonists (LAMAs), antileukotrienes, short-acting beta agonists (SABAs), anticholinergics and monoclonal antibodies.

Further features, details and advantages of the invention arise from the wording of the claims as well as from the following description of exemplary embodiments with the assistance of the drawings.

EXAMPLES

Example 1: Clinical Study "Attenuation of Allergen-Induced Asthmatic Responses by Inhaled GATA-3 Specific DNAzyme"

Abstract
Background
The most prevalent phenotype of asthma is characterized by a TH2-driven eosinophil dominated inflammation. Therapeutic targeting of GATA-3, the master transcription factor of the TH2 pathway, may be beneficial. We evaluated safety and efficacy of a novel DNAzyme specifically directed against GATA-3 mRNA (SB010).

Methods

In this randomized, double-blind, placebo-controlled, multicenter clinical trial, patients with allergic asthma with sputum eosinophilia exhibiting a biphasic early and late phase asthmatic response (EAR and LAR) following allergen provocation were assigned to receive 10 mg SB010 (21 evaluable patients) or placebo (19 evaluable patients) by inhalation once daily for days. Allergen challenge was performed before and after treatment. Change in the area under the $FEV_1$ curve (AUC) in LAR was the primary endpoint.

Results

After 28 days of treatment SB010 attenuated the mean LAR AUC by 34% compared to pretreatment, while a 1% increase of LAR AUC was observed in the placebo group (P=0.02)-EAR AUC was attenuated by 11% by SB010, versus a 10% increase after placebo (P=0.03). These effects were more pronounced in pre-specified subgroups of patients with blood eosinophilia ≥4% (improvement LAR 41.7%, P=0.05; improvement EAR 28.3%, P=0.02) or FeNO ≥40 ppb. Inhibition of LAR by SB010 was associated with attenuation of allergen induced sputum eosinophilia (P=0.06 whole group; P=0.009 eosinophil subgroup; P=0.02 FeNO subgroup), lower sputum tryptase (P=0.05) and plasma IL-5 levels (P=0.05). Allergen induced FeNO levels and airway hyper-responsiveness to methacholine were not affected by treatment.

Conclusions

SB010 treatment significantly attenuated both LAR and EAR in allergic asthma following allergen provocation. Biomarker analysis confirmed a pronounced effect on TH2 regulated inflammatory responses (Clinical Trials—gov number, NCT 01743768).

Introduction

The central core of the active drug product of SB010 represents the catalytic domain which accounts for cleavage of the target following binding of hgd40 to the GATA-3 mRNA[10] (see Figures S1 and S2 in the Supplementary Appendix). Sel et al.[11] reported the development of DNAzymes able to cleave GATA-3 mRNA and demonstrated their efficacy in preclinical models of allergic airway inflammation. The drug substance, hgd40, is characterized by high bioactivity and bioavailability at the site of drug delivery by inhalation[12] and was thus chosen for further clinical development; hgd40 significantly reduced GATA-3 mRNA and protein as well as subsequently the production of TH2 cytokines in human T-cells and tissue explants (Figure S3, Supplementary Appendix). Unwanted off-target effects were excluded[13] and no major safety concerns were identified in an extensive toxicology program[14]. The corresponding drug product, SB010, was investigated in three recently completed randomized, placebo controlled, dose escalation phase I trials (manuscript in revision). The promising results justified a phase IIa trial to assess the efficacy of SB010. This study represents the first phase IIa trial of an inhaled DNAzyme to date.

Methods

Study Design and Oversight

This randomized, double-blind, placebo-controlled study was conducted at 7 study sites specialized in respiratory research in Germany between January (first patient enrolled) and October 2013 (last patient last visit). After screening and baseline assessments, participants were randomized using a centrally generated randomization list (Inamed GmbH, Munich, Germany) with no stratification to a 4-week treatment period of active treatment or placebo. Three inhaled allergen challenges were performed at screening (eligibility), prior to randomization (pre-treatment) and at day 28 (post-treatment). The trial was approved by the German regulatory agency "Bundesinstitut für Arzneimittel and Medizinprodukte (BfArM)" and by central and local ethics committees at each participating center prior to start. The study was conducted according to the principles of good clinical practice and the Declaration of Helsinki. All participants gave their informed consent in writing before any study-specific procedures were performed. Data were collected at each study site and entered into data base at INAMED GmbH (Gauting, Germany). Statistical analysis was independently performed by FGK Clinical Research GmbH (Munich, Germany). The first draft of the manuscript was prepared by the first and last authors, who also made the decision to submit the manuscript for publication. A professional medical writer funded by the sponsor supported in writing and editing. The first and last authors, and the authors who are employees of the sponsor, vouch for the accuracy and completeness of the data, the statistical analysis and the fidelity of the trial to the final protocol.

Patients

We recruited Caucasian male patients aged between 18 and 64 years, who had been diagnosed with mild asthma according to the GINA guidelines[15] at least 6 months prior to screening and who were not treated with any asthma medications other than inhaled short acting bronchodilators. At screening, $FEV_1$ had to be ≥70% of predicted normal at least 6 hours after any intake of short-acting bronchodilators. The allergic nature of their asthma had to be demonstrated through a positive skin prick test to common aeroallergens and positive allergen-induced early- and late-phase response (≥20% and ≥15% decline in $FEV_1$, respectively). Presence of sputum eosinophils had to be demonstrated either before or after screening allergen challenge. Full details of the inclusion and exclusion criteria can be found in the Supplementary Appendix.

Study Treatments

The drug product SB010 was 10 mg human GATA-3-specific DNAzyme hgd40 (manufactured by BioSpring GmbH, Frankfurt, Germany) in 2 mL phosphate buffered saline (or matching placebo). Final drug products were prepared centrally (BAG Health Care GmbH, Lich, Germany) with identical packaging to ensure blinding. Drug product or placebo was administered once daily in the morning by flow- and volume controlled inhalation lasting approximately 3-8 minutes for 28 consecutive days using an $AKITA^2$ APIXNEB nebulizer (Activaero GmbH, Gemünden, Germany) to ensure optimized drug deposition[16]. Prior to enrolment, patients received mandatory training in use of the device. At each visit during the treatment period, active treatment or placebo was administered at the study site under supervision of the study staff. The remaining doses were self-administered and compliance was checked using the smart card of the device.

Study Procedures

An overview of the main study procedures and interventions is shown in FIG. 1A (a full summary of study procedures can be found in the Supplementary Appendix).

Allergen Challenge and Pulmonary Function Testing

The appropriate allergen for allergen challenge was identified by a skin prick test at the first screening visit (for details see Table S1 in the Supplementary Appendix). A subsequent skin prick dilution test at the second screening visit (at least 1 week after the first) in conjunction with airway responsiveness (by methacholine provocation) was used to define a safe starting concentration for the screening allergen challenge[17]. Increasing concentrations of inhaled aeroallergen were administered until a ≥20% decrease in $FEV_1$ was reached[18]. The last three concentration steps of inhaled aeroallergen that led to a 20% decrease in $FEV_1$ were administered before randomization (pre-treatment) and after the 28-day treatment period (post-treatment) in identical manner[19]. Serial spirometry measurements were performed in duplicate between 10 and 180 minutes (early phase asthmatic response, EAR) and between and 7 hours (late phase asthmatic response, LAR) after allergen challenge according to recent guidelines[20]. Appropriate washout times between challenges were implemented to ensure $FEV_1$ and FeNO levels had returned to baseline values in all patients prior to further challenges.

Methacholine Challenge Testing

Airway responsiveness was assessed at the times indicated in FIG. 1A as the concentration of methacholine (Provocholine, Metapharm Inc., Brantford, ON, Canada) leading to a ≥20% decline in $FEV_1$ (the PC20 concentration) according to ATS guidelines[21].

Exhaled Nitric Oxide Measurement

Levels of fractional expiratory nitric oxide (FeNO) were measured at the times indicated in FIG. 1A using the hand-held NIOX MINO® device (Aerocrine, Solna, Sweden) in line with ATS/ERS recommendations[22] according to the manufacturer's instructions.

Sputum Induction

Induced sputum samples were taken at five time-points (FIG. 1A): at screening, before (up to two weeks) and 24 h after pre-treatment challenge, and before (24-48 h) and 24 h after post-treatment. Cell distribution and analysis of mediators in the supernatant were assessed in a central laboratory.

Measurement of Immunological Parameters

The cytokines and chemokines TNF-α, IL-1β, IL-8 MCP-1, MCP-4, MIP-1β, MDC, IP10 and IL-4, IL-5 and IL-13, and IFN-γ were measured in plasma and/or sputum supernatants with a TH1/TH2 and chemokine multiplex assay (Meso Scale Discovery, Rockville, USA) according to the manufacturer's instruction. Eosinophil cationic protein (ECP) and tryptase in sputum supernatants were measured using commercially available ELISA (ECP and tryptase: Cloud—Clone, Houston, USA) according to the manufacturer's instructions.

Safety Assessments

Adverse events and concomitant medication were assessed at every visit. Safety laboratory analyses (including hematology, clinical chemistry and urinalysis) were performed prior to the first administration and at two-week intervals during treatment (details see Supplementary Appendix). Additionally, antinuclear antibodies (immunofluorescence screening test) and rheumatoid serology (IgM) were measured before and after treatment in order to exclude (auto-)antibody development due to treatment with a DNAzyme-based drug.

Study Outcome Measures

The primary outcome measure was the influence of multiple doses of inhaled SB010 on the area under the $FEV_1$ curve (AUC) expressed as percentage of baseline $FEV_1$ during LAR (4—hours after allergen challenge). AUC was calculated using the trapezoidal rule. Exploratory endpoints included influence of SB010 on the area under the $FEV_1$ curve during EAR (0-3 hours), allergen-induced changes in airway responsiveness (PC20 methacholine), FeNO levels, and biomarkers in plasma and sputum.

Sample Size and Statistical Analysis

At least 38 evaluable subjects were required assuming a type I error probability of 10%, difference in effect size between treatment groups of 8%, and power of at least 80%. Based on an anticipated drop-out rate of 15%, 43 subjects were randomized and exposed to trial medication or placebo. Efficacy and pharmacodynamic outcomes were analyzed in all evaluable patients (intention-to-treat population) as indicated in FIG. 1.

The primary efficacy outcome (AUC in LAR) was compared between treatment groups using an ANCOVA model with baseline AUC in LAR as covariate. Four patients in the SB010 group and three patients in the placebo group demonstrated LAR only in the first pretreatment allergen challenge. For these patients, lung function data from this allergen challenge were used as pre-treatment value. Other endpoints were also analyzed with the same model or using Wilcoxon rank sum tests for between group comparisons of percent changes as defined in the statistical analysis plan. Safety outcome measures were listed by patient and descriptive statistics were calculated. Further details of the statistical methods can be found in the Supplementary Appendix.

Results

Patients

Twenty-one patients completed all study assessments in the SB010 group and 18 and 19 patients, respectively, completed LAR and EAR assessments in the placebo group (FIG. 1B). The demographic and baseline data for these patients are shown in Table 1A and Table 1B.

Asthmatic Early and Late Phase Response

Figure 2A:
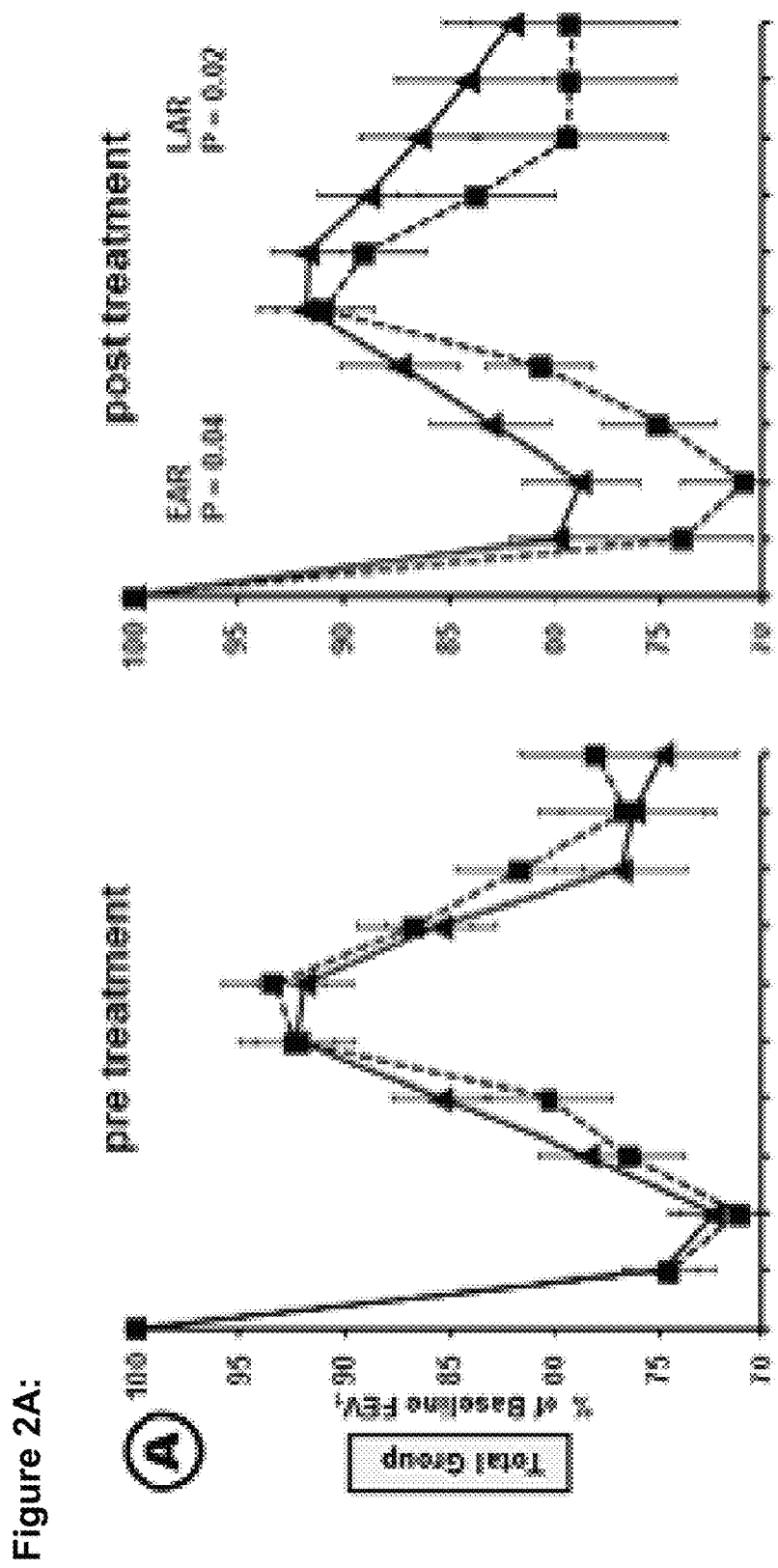
FIG. 2A: Shown are $FEV_1$ levels as a percentage of baseline $FEV_1$ following allergen challenges. Allergen challenges were performed before the treatment period ( ) and after completion of the 4-weeks treatment period ( ). Lung function was recorded for seven hours after allergen challenge. Depicted are mean values per treatment group+/−SEM. Treatment with SB010 (▲) significantly attenuated the early phase asthmatic response (P=0.04, Wilcoxon rank sum test) as well as the late phase asthmatic response (P=0.02, ANCOVA) compared to placebo (■). Results for the study group as a whole are shown in panel A; pre-specified subgroups with blood eosinophils ≥4% (panel B) and FeNO ≥40 ppb (panel C). Blood eosinophils and FeNO levels were measured before randomization. Both subgroups consist of 12 SB010/12 placebo patients, with 9 patients in the SB010 group and 11 patients in the placebo group present in both subgroups. EAR and LAR both improved significantly in the blood eosinophils ≥4% subgroup (P=0.02 and P=0.05 respectively) and in the FeNO ≥40 ppb subgroup (P=0.02 and P=0.05 respectively). Please note: spread x-axis for the first hour following allergen challenge is enlarged.

As shown in FIG. 2A (Supplementary Appendix Table S2), LAR was attenuated following SB010 treatment, with a significant improvement of the mean area under the curve (AUC) of 33.7% (P=0.02) and improvement in maximal $FEV_1$ decline of 31.6% (P=0.09). EAR was also significantly attenuated with a mean AUC improvement of 11.3% (P=0.04) and an improvement of maximum $FEV_1$ decline by 21.5% (P=0.04).

Asthmatic Early and Late Phase Responses in Pre-Specified Subgroups

Figure 2B:
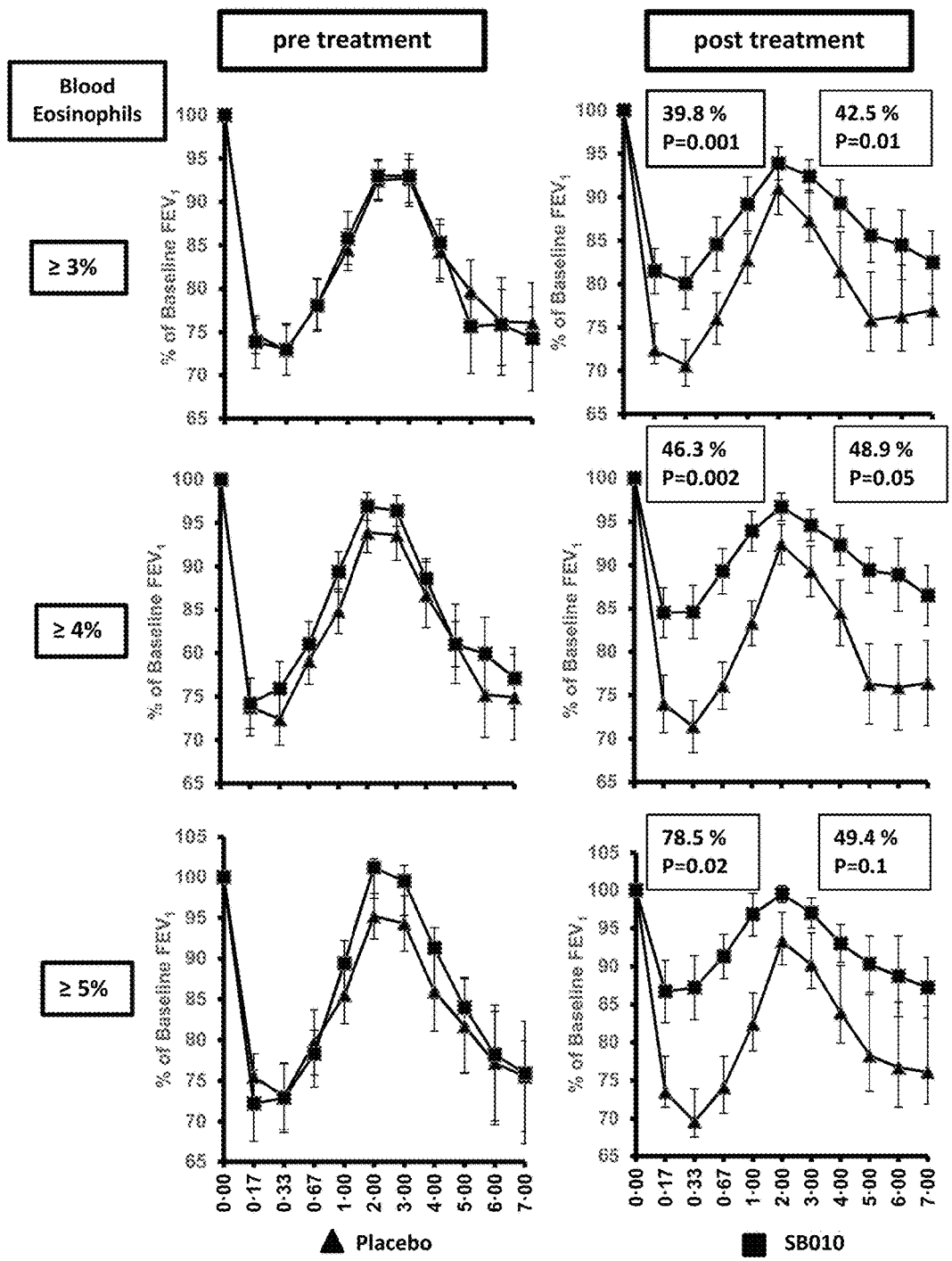
FIG. 2B: Lung function is expressed as percent of baseline FEV1 over time. Shown are separate pre-treatment and post-treatment curves for SB010 and placebo treatment for the three subgroups with blood eosinophils ≥3%, ≥4% and ≥5%, respectively. Depicted are mean values per treatment group plus/minus SEM. Insert boxes indicate the % improvement of the area under the FEV1 curve (AUC) in the SB010 treatment group as compared to placebo for the early phase response (left box) and the late phase response (right box). Statistical analysis by ANCOVA. Please note: X-axis stretched to different scale for the first hour post allergen challenge. Continuous improvement of lung function based on baseline blood eosinophil counts.
Figure 2C:
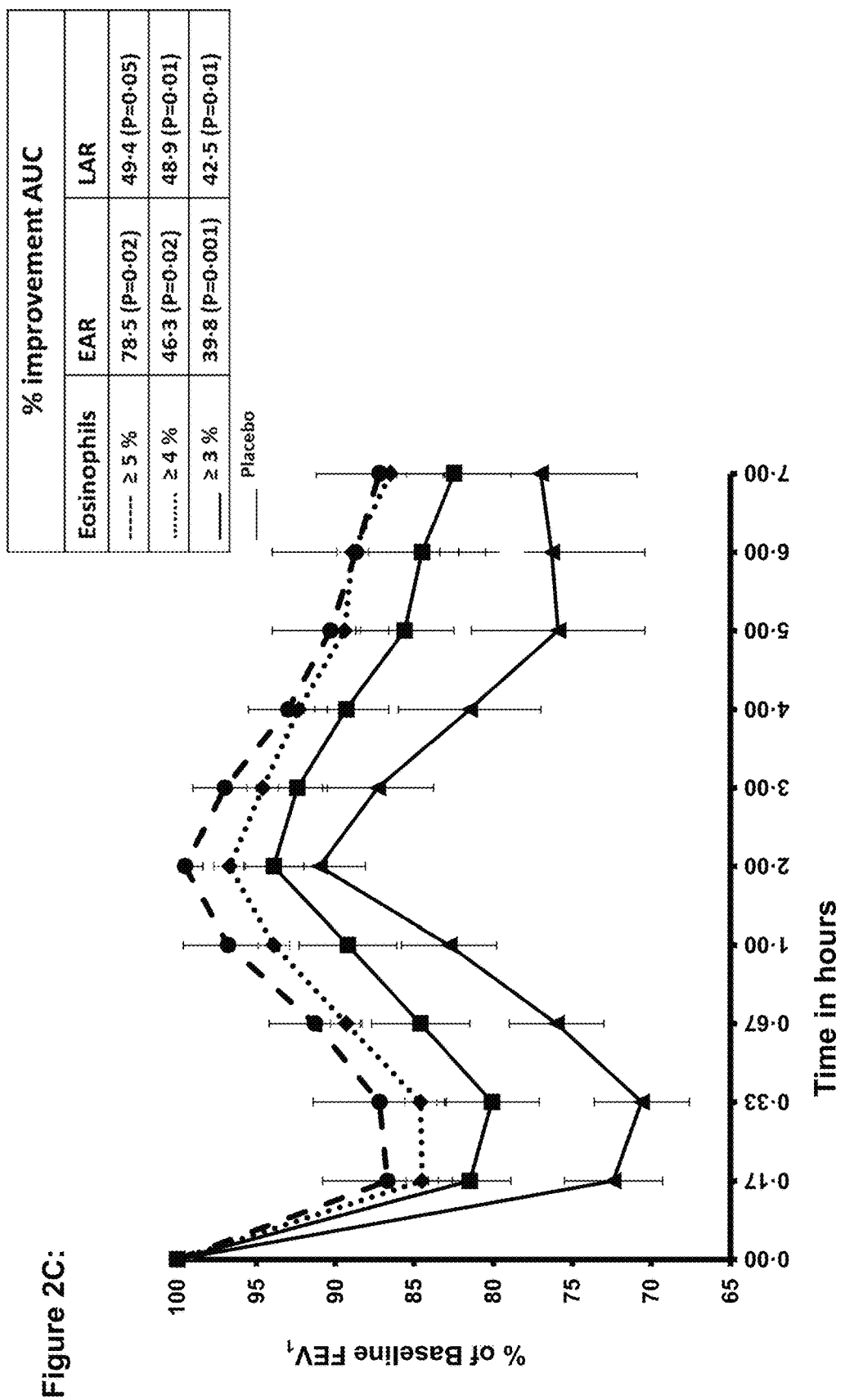
FIG. 2C: Here, the responses to allergen challenges after 28 day treatment with SB010 are shown combined for all three subgroups stratified on baseline blood eosinophil counts. For comparison the post-treatment placebo response for the blood eosinophil ≥3% subgroup is shown which does not significantly differ from placebo responses in the other two subgroups. For further details see legend to FIG. 2.
Figure 3:
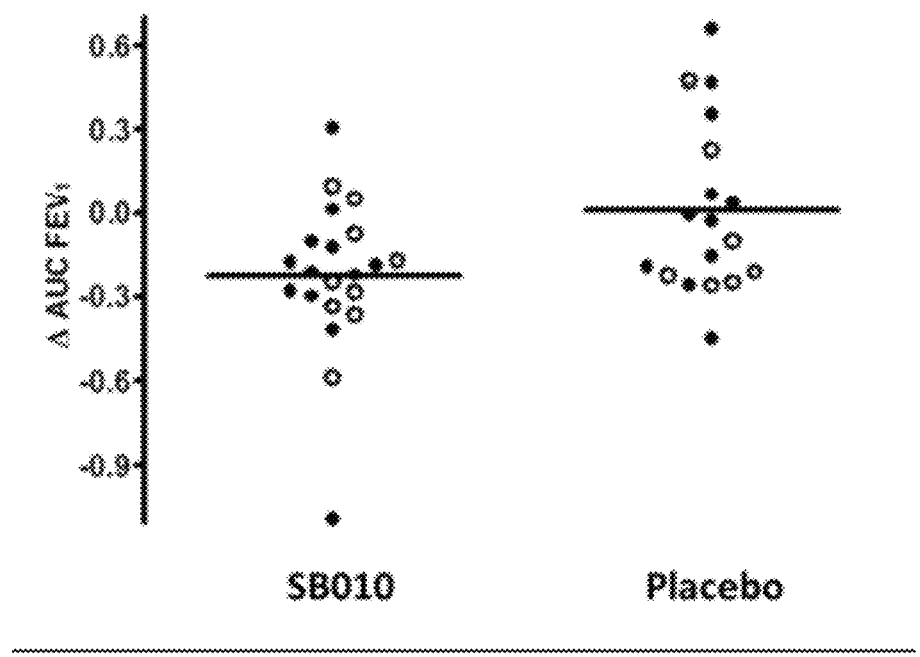
FIG. 3 shows the individual absolute change in the area under the curve (AUC) during late asthmatic responses (LAR). For each patient in the SB010 treatment group (n=21) and the placebo group (n=18) the absolute change in the AUC value during late phase responses (LAR) was calculated and depicted. The line represents the mean; black points: patients with blood eosinophil counts ≥4% at baseline; circles: patients with blood eosinophil counts <4% at baseline. LAR responses do not significantly differ between these two subgroups. For the whole group SB010 treatment significantly attenuated the late phase asthmatic response (P=0.02, FIG. 2). Individual data points see Supplementary Appendix Tables S4A and S4B.

In pre-specified subgroups, patients with relative blood eosinophil counts ≥4% at baseline showed greater improvement in AUC in LAR and a pronounced effect on EAR following SB010 treatment (FIG. 2B and Supplementary Appendix S3A). The decline in AUC in LAR was attenuated in the SB010 group by 41.7% (P=0.05) (Table S3A). This was accompanied by a 28.3% attenuation in EAR (P=0.02). The individual changes in the AUC following SB010 and placebo treatment are depicted in FIG. 3 (and Supplementary Appendix Tables S4A and S4B). Similar observations were reported for the subgroup with FeNO ≥40 ppb at baseline (FIG. 2C, Supplementary Appendix Table S3B). Tests for heterogeneity between strata of the subgroups were not significant.

Interference with Markers of TH2-Driven Inflammation

Figure 4:
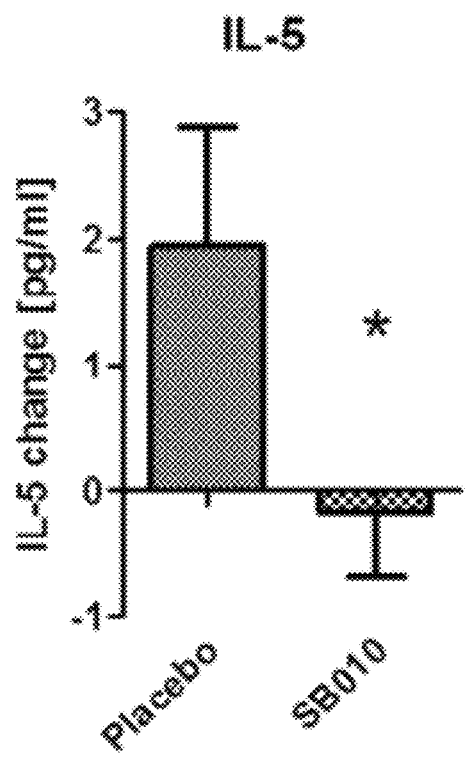
FIG. 4 shows the change in plasma IL-5 levels following allergen challenge before and after treatment with SB010 or placebo. Shown are means±SEM of absolute changes in plasma IL-5 concentrations of patients that exhibited detectable plasma IL-5 levels in response to pre-treatment allergen challenge which were 4.21±1.51pg/ml in the SB010 group (13 patients) and 4.03±0.92pg/ml in the placebo group (12 patients), respectively. The difference is statistically significant with P=0.05 (*).

After 28 days of treatment, SB010 attenuated the allergen induced sputum eosinophilia versus placebo, although this difference missed statistical significance in the whole study group (P=0.06), but became significant in the pre-specified subgroups for blood eosinophils ≥4% (P=0.009) and for FeNO ≥40 ppb (P=0.02). Changes in sputum eosinophilia were accompanied by a significant difference (P=0.05) in blood IL-5 levels (FIG. 4). The post treatment increase in IL-5 levels observed in the placebo group was absent following SB010 treatment. At the end of the 28 day treatment course, sputum tryptase levels were significantly (P=0.05) lower in the SB010 treatment group (median 6.39 IQR 2.03-13.88 ng/mL) as compared to placebo (median 13.10 IQR 6.05-22.77 ng/mL). Allergen-induced FeNO levels and airway hyper-responsiveness to methacholine 24 h post challenge remained unaffected by study treatment (Supplementary Appendix Table S5).

Safety and Tolerability

No noteworthy differences in treatment emergent adverse events (TEAEs) were observed between patients receiving SB010 or placebo. In the placebo group 8 patients had TEAEs as compared to 6 patients in the SB010 group (Table 3). There were no serious TEAEs, nor any probably or certainly SB010-related TEAEs. Two TEAEs (nausea and pruritus) in two patients were possibly related to SB010. There were no serious TEAEs. The other safety variables did not reveal any safety concerns, including all safety endpoints listed in the Supplementary Appendix. The pre- and post-treatment measurements of TNF-α, IL-1β, IL-8, MCP-1, MCP-4, MIP-1β, MDC and IP-10 revealed no significant differences between the study groups (Supplementary Appendix Table S7); neither were significant increases in rheumatoid serology and antinuclear antibodies detected, altogether indicating the absence of innate immune activation and the absence of off-target effects.

Discussion

Inhaled bronchial allergen challenge is a widely accepted in-vivo model of allergic inflammation and bronchoconstriction18, and therapeutic inhibition of LAR in early clinical phase trials is a reasonably good predictor for clinical efficacy in later stages of the drug development program[24]. Examples include targeting pathways of TH2 cytokines such as IL-4[25,26,27], IL-5[28,29,30], IL-13[31,32], and TSLP[33]. In this study, treatment with SB010 significantly improved lung function during both EAR and LAR following allergen inhalation. Since SB010 specifically and selectively targets the transcription factor GATA-3, these data strongly support the importance of GATA-3 dependent and regulated pathways in the asthmatic response after allergen inhalation in patients with a TH2-driven asthma phenotype[6] and suggest that SB010 may represent a promising treatment for allergic asthma.

Our patients had mild allergic asthma with a typical TH2-driven endotype as indicated by elevated blood and sputum eosinophils as well as elevated levels of FeNO[34,35]. This type-2 endotype is not only present in prototypic atopic and allergic asthma, but has also recently been observed in other clinical phenotypes of asthma, including hyper-eosinophilic late onset asthma, persistent and severe asthma, and Aspirin-sensitive asthma[5,36,37]. The inclusion criteria were defined to cover a broader spectrum of patients with this endotype (e.g. just "presence of sputum eosinophils"), and the lung function data show that SB010 had a significant effect on this study group as a whole. However, in a pre-specified subgroup analysis, patients with a more pronounced TH2-driven phenotype (blood eosinophil levels of at least 4% or FeNO levels of at least 40 ppb) appeared to specifically benefit from SB010 treatment. In addition to a more pronounced therapeutic effect on LAR, EAR also showed a significant attenuation. This dual mode of action across both phases of the asthmatic response has not been reported for any biological drug candidate since anti-IgE[38] and most recently anti-TSLP[33]. Whether SB010 treatment may be particularly beneficial for patients prone to severe exacerbations needs to be investigated in upcoming clinical trials[36]. The central role of GATA-3 in the regulation of the TH2 response is well established. Both, development and maintenance of TH2 effector functions strictly depend on GATA-3[39]. More recently, an essential function of GATA-3 has been identified in type 2 innate lymphoid cells[40]. However, this transcription factors also exert important functions well beyond the TH2-cell subset. GATA-3 is also expressed in mast-cells[39], eosinophils[41] and airway epithelial cells, where it controls important functions and effector mechanisms connected with the allergen-induced allergic response[42,43]. Following allergen challenge, EAR depends on mast-cell degranulation, whereas LAR is considered to be preferentially T-cell dependent and accompanied by a marked influx of eosinophils into the airways and airway lumen. Mast-cell tryptase represents a reliable and robust marker reflecting mast-cell activation and mast-cell degranulation. The present results indicate that SB010 treatment directly or indirectly affects these effector cells of the asthmatic response. It is likely that SB010 performs this inhibitory and modulatory function in a dual fashion, both by modulating TH2 cells and thus depriving the effector cells of survival and activation factors, as well as through a direct interference with GATA-3 mRNA in eosinophils and mast-cells in the local inflamed tissue, however, further mechanistic studies are needed to fully elucidate all biological effects of GATA-3 DNAzyme treatment.

The patients exposed in this study, combined with individuals exposed during the phase I program, comprise a safety database of more than 1200 applications in over 120 individuals, 39 of whom had asthma. No safety signals have so far been detected during clinical development, in line with the results of the extensive non-clinical program. In conclusion, this proof-of-concept trial provides evidence of efficacy of inhaled DNAzyme SB010 treatment, which significantly attenuated both the early and late phase asthmatic responses following allergen provocation. Further clinical studies are warranted to explore whether these effects translate into clinical benefits in symptomatic, persistent asthmatics with a predominant TH2 phenotype.

TABLE 1A

Demographic and baseline data for patients completing the study

|  | SB010 (n = 21) | Placebo (n = 19) | P values |
|---|---|---|---|
| Age (years) | 33.8 (9.4) | 38.5 (12.1) | 0.24 |
| Body mass index (kg/m$^2$) | 26.7 (4.2) | 25.6 (3.2) | 0.81 |
| Baseline FEV$_1$ |  |  |  |
| % of predicted | 91.8 (11.6) | 91.9 (12.9) | 0.95 |
| Absolute value (L) | 3.8 (0.7) | 3.8 (0.6) | 0.87 |
| FeNO (ppb) | 49.3 (22.5) | 51.6 (47.1) | 0.34 |
| PC$_{20}$ (mg/dL) | 3.2 (4.2) | 2.8 (4.0) | 0.83 |
| Eosinophils in sputum (median) |  |  |  |
| Differential, % | 3.7 (1.5; 12.1) | 2.4 (1.3; 13.3) | 0.75 |
| Eosinophils in blood (mean) |  |  |  |
| Absolute count (10$^6$/L) | 282.4 (245.8) | 262.8 (173.6) | 0.91 |
| Differential, % | 4.9 (4.0) | 4.5 (3.2) | 0.97 |

All data expressed as mean (SD), except eosinophils in sputum (median, 1st and 3rd quartile). Fractional expiratory nitric oxide (FeNO), airway hyper-reactivity (PC20), blood eosinophils and eosinophils in induced sputum were measured prior to randomization. Eosinophils in sputum values based on n=20 for SB010 and n=17 for placebo group, respectively. P values according to Wilcoxon rank sum test (see Material and Methods).

TABLE 1B

Detailed demographic and baseline data for patients completing the study

| | Blood eosinophils ≥3% | | | Blood eosinophils ≥4% | | | Blood eosinophils ≥5% | | |
|---|---|---|---|---|---|---|---|---|---|
| | Placebo | SB010 | P value | Placebo | SB010 | P value | Placebo | SB010 | P value |
| Age (years) | 36.4 (12.3) | 33.8 (9.8) | 0.6121 | 35.0 (12.3) | 33.3 (11.0) | 0.8395 | 33.4 (12.0) | 32.4 (12.8) | 0.8096 |
| Body mass index (kg/m$^2$) | 25.41 (3.17) | 26.39 (3.44) | 0.8141 | 24.77 (3.21) | 26.68 (3.85) | 0.3406 | 23.49 (2.52) | 25.29 (2.67) | 0.2685 |
| Baseline-FEV$_1$ (% of predicted) | 88.3 (12.0) | 92.9 (12.1) | 0.2699 | 90.2 (11.9) | 93.0 (11.9) | 0.5635 | 89.6 (8.6) | 95.3 (11.5) | 0.3862 |
| Baseline-FEV$_1$ (Absolute value (L)) | 3.727 (0.691) | 3.874 (0.711) | 0.4808 | 3.860 (0.664) | 3.854 (0.730) | 0.9310 | 3.937 (0.616) | 3.941 (0.718) | 0.9616 |
| FeNO (ppb) | 58.01 (51.20) | 52.24 (22.55) | 0.5752 | 68.03 (52.60) | 59.14 (22.30) | 0.5444 | 76.72 (58.85) | 66.79 (19.88) | 0.4705 |
| PC$_{20}$ (mg/dL) | 1.609 (1.840) | 3.082 (4.040) | 0.3660 | 1.774 (1.997) | 3.476 (4.858) | 0.7290 | 1.657 (2.099) | 1.781 (1.972) | 0.9233 |
| Eosinophils (absolute) in blood (10$^6$/L) | 325.4 (128.7) | 349.5 (280.8) | 0.8033 | 358.7 (125.6) | 446.6 (299.5) | 0.5230 | 389.4 (139.2) | 488.8 (340.6) | 0.7144 |
| Eosinophils in blood (%) | 5.10 (3.25) | 5.42 (4.07) | 0.9711 | 5.64 (3.42) | 6.88 (4.26) | 0.4881 | 5.96 (3.94) | 7.73 (4.98) | 0.4699 |

All data expressed as mean (SD).
Fractional expiratory nitric oxide (FeNO), airway hyperreactivity (PC20), blood eosinophils and eosinophils in induced sputum were measured prior to randomization.
P values according to Wilcoxon rank sum test (see Material and Methods).

TABLE 2

Changes in the late and early phase response following allergen challenge before and after treatment

| | SB010 | | Placebo | | Changes In Lung Function | | | | |
|---|---|---|---|---|---|---|---|---|---|
| | | | | | Absolute Change | | Percentage Change | | |
| | Pre-Treatment | Post-Treatment | Pre-Treatment | Post-Treatment | SB010 | Placebo | SB010 | Placebo | P Value |
| LAR | | | | | | | | | |
| AUC [ln h] | 66.4 | 44.0 | 59.2 | 60.0 | 22.4 | -0.8 | 33.7% | -1.4% | P = 0.02 |
| Maximum Decline [ln %] | 30.1 | 20.6 | 29.5 | 26.3 | 9.5 | 3.2 | 31.6% | 10.8% | P = 0.09 |
| EAR | | | | | | | | | |
| AUC [ln h] | 37.9 | 33.6 | 41.1 | 45.4 | 4.3 | -4.3 | 11.3% | -10.5% | P = 0.04 |
| Maximum Decline [ln %] | 30.3 | 23.8 | 33.1 | 31.9 | 6.5 | 1.2 | 21.5% | 3.6% | P = 0.04 |

Shown are the mean values for the area under the curve (AUC) for the late asthmatic response (LAR) and the early asthmatic response (EAR). Decrease in AUC values from pre- to post-treatment reflects an improvement in lung function. Given are the AUC pre- and post-treatment values, followed by the changes in lung function for the SB010 and the placebo group, respectively. These changes are presented as the pre-post values of AUC and as a percent change between pre- and post-treatment. Positive values reflect an improvement in lung function, negative values correspond to a larger area under the curve in the post-treatment challenge compared to pre-treatment. Complete data set see Table S2 in the Supplementary Appendix.

TABLE 3

Treatment emergent adverse events (TEAEs) by system organ class Organ systems

| | Treatment Group | | | |
|---|---|---|---|---|
| | SB010 (n = 21) | | Placebo (n = 19) | |
| Organ systems | Number of TEAEs | Number of patients | Number of TEAEs | Number of patients |
| Ear and labyrinth disorders[1] | 1 | 1 (4.5%) | 0 | 0 (0%) |
| Gastrointestinal disorders[2] | 1 | 1 (4.5%) | 1 | 1 (4.8%) |

TABLE 3-continued

Treatment emergent adverse events (TEAEs) by system organ class Organ systems

| | Treatment Group | | | |
|---|---|---|---|---|
| | SB010 (n = 21) | | Placebo (n = 19) | |
| Organ systems | Number of TEAEs | Number of patients | Number of TEAEs | Number of patients |
| Infections and Infestations[3] | 4 | 3 (13.6%) | 2 | 2 (9.5%) |
| Injury, poisoning and procedural complications[4] | 0 | 0 (0%) | 1 | 1 (4.8%) |
| Musculoskeletal and connective tissue disorders[5] | 1 | 1 (4.5%) | 0 | 0 (0%) |
| Nervous system disorders[6] | 5 | 3 (13.6%) | 2 | 2 (9.5%) |
| Respiratory, thoracic and mediastinal disorders[7] | 3 | 3 (13.6%) | 5 | 4 (19%) |
| Skin and subcutaneous tissue disorders[8] | 1 | 1 (4.5%) | 0 | 0 (0%) |

[1] vertigo;
[2] diarrhea, nausea;
[3] herpes simplex, nasopharyngitis;
[4] laceration;
[5] myalgia;
[6] headache, sciatica;
[7] asthma, bronchial obstruction, dyspnea, increased upper airway secretion, oropharyngeal pain, upper-airway cough syndrome;
[8] pruritus.

Supplementary Appendix: Attenuation of Allergen-Induced Asthmatic Responses by Inhaled GATA-3 Specific DNAzyme Material and Methods Inclusion and Exclusion Criteria Inclusion Criteria 1. Adult male Caucasian patients aged ≥18 and ≥60 years,
2. Clinical diagnosis of mild asthma (according to GINA guidelines 2008) for at least 6 months prior to screening. No concomitant asthma treatment, except inhaled short 75 acting bronchodilators,
3. Screening $FEV_1$ value of $FEV_1 \geq 70\%$ of the predicted normal value (ECSC) after a wash out of at least 6 hours for inhaled short-acting bronchodilators,
4. Patient must demonstrate sufficient induced sputum production,
5. Positive skin prick test (skin reactivity) to common aeroallergens (e.g. animal epithelia, dust mite),
6. Patient must demonstrate positive allergen-induced early- and late-phase airway bronchoconstriction,
7. At all time points before AC and MCh, patients must show $FEV_1$ not below 65% predicted.
8. Presence of sputum eosinophils either before or after screening allergen challenge (first or second induced sputum),
9. Patient has been informed both verbally and in writing about the objectives of the clinical trial, the methods, the anticipated benefits and potential risks and the discomfort to which he may be exposed, and has given written consent to participation in the trial prior to trial start and any trial-related procedure,
10. Patient is able to understand and give written informed consent and has signed a written informed consent form approved by the Investigator's Research Ethics Board,
11. Non-smokers or ex-smokers who had stopped smoking for at least 1 year prior to start of the clinical study with <10 pack years,
12. Ability to inhale in an appropriate manner (patients will be trained to inhale from the AKITA2 APIXNEB® device with a placebo medication at the screening visit).
13. Only men who do not want to father children for six months after the last dose of SB010 will be included into this study.

Exclusion Criteria

1. Presence of clinically significant diseases other than asthma (cardiovascular, renal, Hepatic, gastrointestinal, haematological, neurological, genitourinary, autoimmune, endocrine, metabolic, etc.), which, in the opinion of the investigator, may either put the patient at risk because of participation in the trial, or diseases which may influence the results of the study or the patient's ability to take part in it,
2. Presence of relevant pulmonary diseases or history of thoracic surgery, such as:
known active tuberculosis,
History of interstitial lung or pulmonary thromboembolic disease,
Pulmonary resection during the past 12 months,
History of status asthmaticus,
History of bronchiectasis secondary to respiratory diseases (e.g. cystic fibrosis, Kartagener's syndrome, etc.),
History of chronic bronchitis, emphysema, allergic bronchopulmonary aspergillosis or respiratory infection within the 4 preceding weeks of the first morning IMP administration,
3. Patients on concomitant treatments, except for inhaled short-acting bronchodilators as judged by the investigator,
4. Use of short-acting 132-agonists 6 hours before study visits 2, 3, 4, 5, 11, and 12,
5. Hospitalisation or emergency room treatment for acute asthma in the 6 months prior to screening, between screening and the start of the treatment period,
6. Intubation (ever) or hospitalisation for longer than 24 hours for the management of an asthma exacerbation within the preceding 6 months of the screening visit,
7. History or current evidence of clinically relevant allergies or idiosyncrasy to drugs,
8. History of allergic reactions to any active or inactive ingredients of the nebulizer solution,
9. ECG abnormalities of clinical relevance, 10. Subjects with a resting heart rate <45 bpm, systolic blood pressure <100 mmHg, diastolic blood pressure <60 mmHg, 11. Proneness to orthostatic dysregulation, faintings, or blackouts, 12. History of malignancy within the past 5 years, except excised basaliomas, 13. Clinically relevant abnormalities in clinical chemical, haematological or in any other laboratory variables as judged by the investigator, 14. Clinically relevant acute infections in the last 4 weeks preceding AC, 15. Clinically relevant chronic infections, 16. Positive results in any of the virology tests of acute or chronic infectious human immunodeficiency virus (HIV) and hepatitis B/C virus infections, 17. Positive drug screen, 18. Abuse of alcohol or drugs, 19. Positive cotinine test, 20. Treatment with any known enzyme inducing or inhibiting agents (St. John's Wort (Johanniskraut), barbiturates, phenothiazines, cimetidine, ketoconazole etc.) within 30 days before first administration of trial medication or during treatment period of the trial, 21. Use of any prohibited concomitant medication within 2 weeks (for biologics: 6 months or 10 times the elimination half-life of the respective drug) before first trial medication administration or within <10 times the elimination half-life of the respective drug, or the duration of the pharmacodynamic effect, whatever is longer, or anticipated concomitant medication during the treatment period, 22. Consumption of any enzyme inducing or inhibiting aliments and beverages (e.g. broccoli, Brussels sprout, grapefruit, grapefruit juice, star fruit etc.) within 14 days prior to the first trial medication administration and during the treatment period of the trial, 23. Consumption of any caffeine-containing product 6 hours before first procedure at each study visit 24. Surgery of the gastrointestinal tract which may interfere with drug absorption of swallowed fraction (Note: this is not applicable for minor abdominal surgery such as appendectomy or herniotomy), 25. Blood donation within the last 30 days before screening, 26. Planned donation of germ cells, blood, organs or bone marrow during the course of the trial or within 6 months thereafter, 27. Participation in another clinical trial with an investigational drug or device within the last month or within 10 times the half-life of the respective drug. For biologics the minimum period is at least 6 months or the time of duration of the pharmacodynamics effect or 10 times the half-life of the respective drug before inclusion in this trial, 28. Lack of ability or willingness to give informed consent or inability to cooperate adequately, 29. Anticipated non-availability for trial visits/procedures, 30. Vulnerable subjects (e.g., persons kept in detention), 31. Employee at the investigational site, relative or spouse of the investigator.

In-Vitro Experiments

In-vitro experiments were performed to demonstrate cleavage activity and specificity of the GATA-3 DNAzyme. Bioactivity and mode of action were assessed in cell culture experiments using peripheral blood T-cells and sino-nasal tissue fragments as a model of mucosal airway tissue.

Cleavage Assay (Supplementary Appendix Figure S2)

Analysis of RNA cleaving catalytic activity of DNAzymes was performed using an in vitro cleavage assay as previously described (Sel et al. JACI 2008). Briefly, 2 µl of in vitro transcribed GATA-3 copy(c)RNA (250 ng/µl) were added to a mixture of 4 µl RNAse-free water, 1 µl 1 M NaCl, 1 µl 10 mM $MgCl_2$ and 1 µl 500 mM Tris pH 7.4. One µl of the respective DNAzyme (hgd40, scrambled DNAzymes 1-6 with scrambled binding regions but intact catalytic sequence, transcription factor Tbet-specific DNAzymes 1-3) or water (negative control) was added and the mixture was incubated at 37° C. If not otherwise indicated, DNAzymes were applied at a concentration of 10 µM and the standard incubation time was 60 min. Subsequently, reaction mixes were electrophoretically separated using agarose gels and visualized by ethidium bromide staining using standard procedures.

Patients and Sample Collection (Supplementary Appendix Figure S3, C-F)

Study subjects were selected on the basis of a documented medical history for chronic rhinosinusitis with nasal polyps (CRSwNP), a pathological nasal endoscopy and CT-Scan of the sinuses. Samples from the ethmoidal sinuses were collected from n=16 patients (aged 16-72 yrs with an median age of 44 yrs; 11 males, 5 females; 8 atopics and 10 asthmatics) during functional endoscopic sinus surgery (FESS) procedures, indicated independently from this study, at the Department of Otorhinolaryngology at the Ghent University Hospital, Belgium, according to the current European and American Guidelines. All patients gave informed consent before their participation and the study was approved by the local ethical committee. The use of any oral or topical medication with possible impact on measurements of mediators was stopped in all subjects at least 4 weeks before surgery.

Preparation and Treatment of Sinonasal Tissue Fragments (Supplementary Appendix Figure S3, C and D)

Immediately after surgical removal of nasal polyps from patients, tissue fragments of about 0.9 mm3 each were prepared by cutting sinonasal explants. The tissue fragments were suspended in RPMI-1640 medium and incubated either with tissue culture medium (TCM) alone or 4 mg/ml of DNAzyme hgd40 for 6 (RNA) and 24 hours (protein). Then, tissue fragments and supernatants were snap frozen and stored at −20° C./−80° C. until protein and mRNA analysis. For investigation of DNAzyme hgd40 uptake, tissue fragments were incubated with TCM alone or 4 mg/ml of rhodamine 6G labelled hgd40 in the presence of lipofectamine transfection reagent for 24 hours. Then, tissue fragments were embedded, immediately snap frozen and cut in 5 µm sections. Sections were stained for the CD3 marker according to manufacturer's recommendation. Subsequently, slides were evaluated using confocal laser scanning microscopy.

Generation and Transfection of Polarized Th2 Cells (Supplementary Appendix Figure S3, A and B)

Naïve human CD4+ cells were isolated from whole blood or buffy coats by Ficoll gradient centrifugation and subsequent enrichment using the naïve CD4 T-cell isolation kit (Miltenyi) according to manufacturer's instruction. Isolated cells were polarized to Th2 cells by stimulation with anti-CD3 and anti-CD28 in the presences of IL-2 (20 ng/ml), IL-4 (20 ng/ml) and anti-IFNγ (1 µg/ml) for 10 days, as previously described. After polarization the Th2 cells were transfected with either the FAM-labeled human GATA-3 specific DNAzyme hgd40 or the FAM-labeled scrambled control DNAzyme ODNg3 by electroporation using the Amaxa system. Transfected cells were replated and incubated for 22 h.

GATA-3 Expression Analysis in Polarized Th2 Cells (Supplementary Appendix Figure S3A)

After the incubation period the transfected cells were harvested and analyzed for GATA-3 protein expression by fluorescence flow cytometry (FACS) analysis. Therefore cells were intracellularly stained for GATA-3 protein with an Alexa Fluor 647-labeled mouse anti-GATA-antibody (Clone L50-823, BD Pharmingen) using the "Transcription Factor Staining Buffer Set" (eBioscience) according to manufacturer's instructions. For analysis gates were set on positively transfected cells and GATA-3 expression levels were determined in these cells as geometric mean levels. The geometric mean levels of GATA-3 protein expression in transfected cells as controlled by FAM positivity was compared between the hgd40 transfected and control transfected cells.

GATA-3 Gene Expression in Sinonasal Tissue Fragments (Supplementary Appendix Figure S3E)

After an incubation time of 6 hours, total RNA was extracted by using the Aurum Total RNA Mini Kit (Bio-Rad Laboratories) and cDNA was synthesized with the iScript cDNA synthesis kit (Bio-Rad Laboratories). Real-time PCR amplification was performed with following conditions: 95° C. for 10 minutes, followed by 45 cycles of 30 seconds at 95° C., 30 seconds at 60° C., and 10 second at 72° C., and a dissociation curve analysis from 60° C. to 95° C. β-actin (ACTB), hypoxanthine phosphoribosyltransferase 1, and elongation factor 1 were used as endogenous reference for normalization.

IL-5 Protein Measurement (Supplementary Appendix Figure S3F)

After an incubation period of 24 hrs supernatants were collected, and concentration of IL-5 was measured with the Luminex xMAP Technology by using commercially available Fluorokine MAP Kits (R&D Systems Europe Ltd,) following manufacturer's guidelines and measured on a Bio-Plex 200 Platform (Bio-Rad Laboratories). The detection limit was 1.5 pg/ml.

IL-13 Secretion Assay (Supplementary Appendix Figure S3B)

For analysis of IL-13 release transfected cells were stimulated with 1 µg/ml *Staphylococcus aureus* enterotoxin B (SEB) for 22 h. IL-13 secretion was detected by FACS analysis using the IL-13 secretion assay detection kit (Miltenyi) according to manufacturer's instruction. For analysis gates were set on positively transfected cells, and IL-13 expression levels were determined in these cells as geometric mean levels (GeoMean). The geometric mean levels of IL13 protein expression in transfected cells as controlled by FAM positivity was compared between the hgd40 transfected and control transfected cells.

Safety Endpoints

The following clinical chemistry parameters were assessed: creatinine, alkaline phosphatase, total bilirubin, alanine aminotransferase, aspartate aminotransferase, gamma glutamyl transpeptidase, total protein, uric acid, urea, sodium, potassium, calcium, chloride, glucose (fasting), lactate dehydrogenase, and creatine phosphokinase. The hematological parameters were: hemoglobin, haematocrit, mean corpuscular volume, mean corpuscular hemoglobin, mean corpuscular hemoglobin concentration, red blood cell count, white blood cell count with differential count (neutrophils, eosinophils, basophils, lymphocytes, monocytes), and platelet count, activated partial thromboplastin time, prothrombin time, INR, fibrinogen. The following urinalysis parameters were assessed: leukocytes, nitrite, pH, protein, glucose, ketone, urobilinogen, bilirubin, blood (hemoglobin and erythrocytes). The following ECG parameters were recorded: A 12-lead ECG was recorded after 5 min rest in supine position using the leads according to Einthoven and Goldberger as well as 6 precordial leads according to Wilson.

Statistical Analysis

Statistical analysis was performed using SAS (version 9.3) software by FGK Clinical Research GmbH (Munich, Germany). Figure S2 was prepared using GraphPad Prism (version 5.0) software.

Discussion of Figure S1:

Following allergen exposure airway dendritic cells present allergen to Th0 cells which differentiate to Th2 cells under the influence of epithelial-derived cytokines such as TSLP, IL25, and IL-33 and initial IL-4 (e.g. produced by type 2 innate lymphocytes [ILC2]). GATA-3 represents the master transcription factor for Th2 differentiation and activation and is indispensable for the production of Th2 cytokines, e.g. IL-4, IL-5, IL-13. By release of these cytokines Th2 cells involve several effector mechanisms such as production of IgE by B cells with subsequent binding to mast-cells, recruitment and activation of eosinophils and development of Goblet cell hyperplasia. Mediators released by these effector cells further promote inflammation, lead to smooth muscle contraction and mucus production with subsequent airway narrowing and vascular leakage. SB010 interferes quite up-stream in this process by specifically cleaving the messenger RNA for GATA-3 in Th2 cells. In consequence, less GATA-3 protein is generated which may then not sufficiently transactivate the transcription Th2 cytokines with subsequent inhibition of all down-stream processes. Similar to its action in Th2 cells, SB010 may also suppress GATA-3 production in other GATA-3-expressing cells, such as ILC2, mast-cells and eosinophils with down-stream inhibition of type-2 cytokine release and also effector molecule production in mast-cells and eosinophils. Figure S1 further shows the bioactivity of hgd40—the active compound of SB010. There is clear evidence for direct and specific effects of hgd40, the active GATA-3 DNAzyme in SB010, on GATA-3 expression and downstream biological effects. A series of in vitro and in situ experiments clearly demonstrate the mode of action of SB010 the results of which are included as Figures S2 and S3 (technical details see Supplementary Appendix). Initially specific activity of hgd40, the active GATA-3 DNAzyme in SB010, was shown using the cleavage assay (additional Figure S2) representing a highly specific in-vitro method to determine the catalytic activity of 10-23 DNAzymes. For that, in-vitro transcribed copy-RNA (cRNA)—in the present case human GATA-3 cRNA—is incubated with the DNAzyme. During this incubation, active DNAzymes catalytically cleave a target cRNA into two cleavage products which can be demonstrated by agarose gel electrophoresis. Based on a series of cleavage assay analyses, it turned out that hgd40—the active component in SB010—is the most active DNAzyme with regard to GATA-3 cRNA cleavage activity. hgd40 was shown to dose and time-dependently cleave GATA-3 cRNA (Figures S2A and S2B). Cleavage is highly sequence specific, as demonstrated by analysis of efficacy of non-GATA-3-specific DNAzymes on GATA-3 cRNA (Figure S2C). It was also demonstrated that hgd40 specifically cleaves single stranded RNA even at low concentrations (0.5 µM hgd40) and does not cleave double stranded DNA, even not at high concentrations (20 µM hgd40). Furthermore, unwanted off target effects such as activation of innate immune cells or on cells involved allergic effector mechanisms have been excluded previously (Dicke T et al. *Nucleic Acid Therapeutics* 2012; 22(2):117-26). Subsequently, we demonstrated the bioactivity of this molecule in human cell and tissue material (additional Figure S3). Transfection of human polarized CD4+ TH2-cells with hgd40 significantly suppressed GATA-3 protein expression and subsequent IL-13 production in comparison to cells transfected with a scrambled control DNAzyme ODNg3 (Figures S3A, S3B).

Next, nasal tissue explants obtained from atopic asthmatics were incubated with the hgd40 DNAzyme. As shown in FIGS. 3C and 3D, hgd40 was taken up by CD3+ and CD3− cells within the explant and significantly reduced the levels of GATA-3 mRNA within 6 hours (Figure S3E) accompanied by significantly reduced production of IL-5 at 24 hours (Figure S3F).

SUPPLEMENTARY APPENDIX TABLE S1

| Allergens used for allergen provocation | | | | |
|---|---|---|---|---|
| | SB010 | | Placebo | |
| Name | Number | % | Number | % |
| Cat | 3 | 14% | 2 | 11% |
| Dog | 2 | 10% | 0 | 0% |
| Grass mix | 3 | 14% | 6 | 32% |
| Birch | 6 | 29% | 2 | 11% |
| Rye | 2 | 10% | 4 | 21% |
| *D. pteronyssinus* | 5 | 24% | 4 | 21% |
| Horse | 0 | 0% | 1 | 5% |
| total | 21 | 100% | 19 | 100% |
| o/w seasonal | 11 | 52% | 12 | 63% |
| o/w perennial | 10 | 48% | 7 | 37% |

Allergens supplied by ALK-Abelló Arzneimittel GmbH, Germany, or Allergopharma Joachim Ganzer KG, Germany, in the case of Alternaria tenuis

SUPPLEMENTARY APPENDIX TABLE S2

Changes in the late and early phase response following allergen challenge before and after treatment - Complete set of lung function data

| | SB010 | | Placebo | | Changes in lung function | | | | Group difference | Statistics |
|---|---|---|---|---|---|---|---|---|---|---|
| | Pre | Post | Pre | Post | SB010 | Placebo | SB010 | Placebo | (%) | P value |
| LAR | | | | | | | | | | |
| AUC | | | [h * 100] | | | | [%] | [%] | | |
| Mean | 66.4 | 44.0 | 59.2 | 60.0 | 22.4 | −0.8 | 33.7% | −1.4% | 35.1% | 0.02 |
| Median | 64.2 | 33.1 | 47.2 | 37.2 | 31.1 | 10.0 | 48.4% | 21.2% | 27.2% | |
| Max. Decline | | | | | percentage point | | [%] | [%] | | |
| Mean | 30.1 | 20.6 | 29.5 | 26.3 | 9.5% | 3.2% | 31.6% | 10.8% | 20.8% | 0.09 |
| Median | 30.2 | 15.0 | 22.3 | 22.1 | 15.2% | 0.2% | 50.3% | 0.9% | 49.4% | |
| EAR | | | | | | | | | | |
| AUC | | | [h * 100] | | | | [%] | [%] | | |
| Mean | 37.9 | 33.6 | 41.1 | 45.4 | 4.3 | −4.3 | 11.3% | −10.5% | 21.8% | 0.04 |
| Median | 33.5 | 28.5 | 40.1 | 39.9 | 5.0 | 0.2 | 14.9% | 0.5% | 14.4% | |
| Max. Decline | | | | | percentage point | | [%] | [%] | | |
| Mean | 30.3 | 23.8 | 33.1 | 31.9 | 6.5% | 1.2% | 21.5% | 3.6% | 17.9% | 0.04 |
| Median | 29.3 | 22.9 | 33.9 | 33.1 | 6.4% | 0.8% | 21.8% | 2.4% | 19.4% | |

Legend Table S2: Changes in the Late and Early Phase Response Following Allergen Challenge Before and After Treatment—Complete Set of Lung Function Data Allergen provocations were performed before (pre) and after (post) 28 days of treatment with SB010 or placebo. Shown are the mean values for the area under the curve (AUC) for the late asthmatic response (LAR) and the early asthmatic response (EAR). Decrease in AUC values from pre to post treatment reflects an improvement in lung function. Given are the AUC pre and post treatment values, followed by the changes in lung function for the SB010 and the placebo group, respectively. These changes are presented as the pre-post values of the AUC and as a percent change between pre and post treatment. Positive values reflect an improvement in lung function, negative values correspond to a larger area under the curve in the post treatment challenge compared to pre-treatment. The group difference shows the delta of relative changes between SB010 and placebo group. P values for LAR AUC and maximum $FEV_1$ decline in LAR and EAR were calculated by ANCOVA model; P value for EAR AUC was calculated by Wilcoxon rank sum test.

SUPPLEMENTARY APPENDIX TABLE S3A

Changes in the late and early phase response following allergen challenge before and after treatment - Analysis of pre-specified subgroup of patients with blood eosinophils ≥4%

| | SB010 | | Placebo | | Changes in lung function | | | | Group difference | Statistics |
|---|---|---|---|---|---|---|---|---|---|---|
| | Pre | Post | Pre | Post | SB010 | Placebo | SB010 | Placebo | (%) | P value |
| LAR | | | | | | | | | | |
| AUC | | | [h * 100] | | | | [%] | [%] | | |
| Mean | 55.6 | 32.4 | 62.8 | 67.3 | 23.2 | −04.5 | 41.7% | −7.2% | 48.9% | 0.05 |
| Median | 43.5 | 28.3 | 47.0 | 93.3 | 15.2 | −46.3 | 34.9% | −98.5% | 133.5% | |
| Max. Decline | | | | | percentage point | | [%] | [%] | | |
| Mean | 27.6 | 17.1 | 30.6 | 29.2 | 10.5% | 1.4% | 38.0% | 4.6% | 33.5% | 0.07 |
| Median | 27.5 | 14.2 | 21.6 | 35.6 | 13.3% | −14.0% | 48.4% | −64.8% | 113.2% | |
| EAR | | | | | | | | | | |
| AUC | | | [h * 100] | | | | [%] | [%] | | |
| Mean | 26.5 | 19.0 | 35.5 | 41.9 | 7.5 | −6.4 | 28.3% | −18.0% | 46.3% | 0.02 |
| Median | 26.0 | 18.5 | 36.0 | 44.9 | 7.5 | −8.9 | 28.9% | −24.7% | 53.6% | |
| Max. Decline | | | | | percentage point | | [%] | [%] | | |
| Mean | 28.2 | 19.0 | 29.7 | 30.8 | 9.2% | −1.1% | 32.6% | −3.7% | 36.3% | 0.10 |
| Median | 27.4 | 18.0 | 28.8 | 33.8 | 9.4% | −5.0% | 34.3% | −17.4% | 51.7% | |

Legend Table S3A: Changes in the Late and Early Phase Response Following Allergen Challenge Before and After Treatment—Analysis of Pre-Specified Subgroup of Patients with Blood Eosinophils ≥4%

Allergen provocations were performed before (pre) and after (post) 28 days of treatment with SB010 or placebo. Shown are the mean values for the area under the curve (AUC) for the late asthmatic response (LAR) and the early asthmatic response (EAR). Decrease in AUC values from pre to post treatment reflects an improvement in lung function. Given are the AUC pre and post treatment values, followed by the changes in lung function for the SB010 and the placebo group, respectively. These changes are presented as the pre-post values of the AUC and as a percent change between pre and post treatment. Positive values reflect an improvement in lung function, negative values correspond to a larger area under the curve in the post treatment challenge compared to pre-treatment. The group difference shows the delta of relative changes between SB010 and placebo group. P value for LAR AUC was calculated by ANCOVA model; P values for EAR AUC and maximum $FEV_1$ decline in LAR and EAR were calculated by Wilcoxon rank sum test.

SUPPLEMENTARY APPENDIX TABLE S3B

Changes in the late and early phase response following allergen challenge before and after treatment - Analysis of pre-specified subgroup of patients with FeNO ≥40 ppb

| | SB010 | | Placebo | | Changes in lung function | | | | Group difference | Statistics |
|---|---|---|---|---|---|---|---|---|---|---|
| | Pre | Post | Pre | Post | SB010 | Placebo | SB010 | Placebo | (%) | P value |
| LAR | | | | | | | | | | |
| AUC | | | [h * 100] | | | | [%] | | [%] | |
| Mean | 58.3 | 36.7 | 58.5 | 65.3 | 21.6 | −6.8 | 37.1% | −11.6% | 48.7% | 0.05 |
| Median | 44.6 | 32.4 | 47.0 | 71.6 | 12.2 | −24.6 | 27.4% | −52.3% | 79.6% | |
| Max. Decline | | | | | percentage point | | [%] | | [%] | |
| Mean | 28.0 | 18.0 | 29.8 | 28.3 | 10.1% | 1.5% | 35.7% | 5.0% | 30.7% | 0.08 |
| Median | 22.9 | 14.1 | 21.6 | 26.4 | 8.8% | −4.8% | 38.4% | −22.2% | 60.7% | |
| EAR | | | | | | | | | | |
| AUC | | | [h * 100] | | | | [%] | | [%] | |
| Mean | 26.8 | 22.6 | 35.2 | 43.5 | 4.2 | −8.3 | 15.7% | −23.6% | 39.3% | 0.02 |
| Median | 23.0 | 18.5 | 36.0 | 44.9 | 4.5 | −8.9 | 19.6% | −24.7% | 44.3% | |
| Max. Decline | | | | | percentage point | | [%] | | [%] | |
| Mean | 29.3 | 20.3 | 29.8 | 32.5 | 9.0% | −2.7% | 30.7% | −9.1% | 39.8% | 0.02 |
| Median | 26.6 | 19.3 | 28.8 | 35.0 | 7.3% | −6.2% | 27.4% | −21.5% | 49.0% | |

Legend Table S3B: Changes in the Late and Early Phase Response Following Allergen Challenge Before and After Treatment—Analysis of Pre-Specified Subgroup of Patients with FeNO ≥40 ppb Allergen provocations were performed before (pre) and after (post) 28 days of treatment with SB010 or placebo. Shown are the mean values for the area under the curve (AUC) for the late asthmatic response (LAR) and the early asthmatic response (EAR). Decrease in AUC values from pre to post treatment reflects an improvement in lung function. Given are the AUC pre and post treatment values, followed by the changes in lung function for the SB010 and the placebo group, respectively. These changes are presented as the pre-post values of the AUC and as a percent change between pre and post treatment. Positive values reflect an improvement in lung function, negative values correspond to a larger area under the curve in the post treatment challenge compared to pre-treatment. The group difference shows the delta of relative changes between SB010 and placebo group. P values for LAR AUC and maximum $FEV_1$ decline in LAR and EAR were calculated by ANCOVA model; P value for EAR AUC was calculated by Wilcoxon rank sum test.

SUPPLEMENTARY APPENDIX TABLE S4A

Individual response to allergen challenge, late-phase asthmatic response (LAR, 3-7 h)

| Patient | | Blood Eos | Allergen Used | Pre-Treatment AUC (h) | Post-Treatment AUC (h) | Absolute Change | % Change |
|---|---|---|---|---|---|---|---|
| SB010-Treatment Group | 1 | * | Birch pollen | 0.94 | 0.66 | −0.28 | −29.6% |
| | 2 | | Birch pollen | 1.33 | 0.99 | −0.33 | −25.2% |
| | 3 | * | Cat | 1.25 | 0.83 | −0.42 | −33.6% |
| | 4 | | Grass pollen | 0.45 | 0.37 | −0.08 | −17.3% |
| | 5 | * | House dust mite | 0.32 | 0.13 | −0.19 | −59.8% |
| | 6 | * | Dog | 0.92 | −0.17 | −1.09 | −119.0% |
| | 7 | * | Cat | 0.68 | 0.47 | −0.21 | −31.2% |
| | 8 | * | Birch pollen | 0.43 | 0.25 | −0.18 | −41.6% |
| | 9 | | Grass pollen | 0.66 | 0.49 | −0.17 | −26.1% |
| | 10 | | House dust mite | 0.59 | 0.22 | −0.37 | −62.1% |
| | 11 | * | Grass pollen | 0.03 | 0.33 | 0.31 | 1224.0% |
| | 12 | | House dust mite | 0.36 | 0.08 | −0.28 | −77.5% |
| | 13 | | House dust mite | 0.95 | 1.00 | 0.05 | 5.5% |
| | 14 | * | House dust mite | 0.44 | 0.32 | −0.13 | −28.3% |
| | 15 | | Birch pollen | 1.63 | 1.39 | −0.25 | −15.1% |
| | 16 | | Birch pollen | 0.64 | 0.74 | 0.10 | 15.3% |
| | 17 | * | Cat | 0.18 | 0.07 | −0.10 | −58.2% |

SUPPLEMENTARY APPENDIX TABLE S4A-continued

Individual response to allergen challenge, late-phase asthmatic response (LAR, 3-7 h)

|  |  |  |  | AUC (h) | | | |
|---|---|---|---|---|---|---|---|
| Patient | | Blood Eos | Allergen Used | Pre-Treatment | Post-Treatment | Absolute Change | % Change |
| | 18 | * | Birch pollen | 0.76 | 0.77 | 0.01 | 1.6% |
| | 19 | | Dog | 0.66 | 0.07 | −0.59 | −89.5% |
| | 20 | * | Rye | 0.32 | 0.10 | −0.22 | −68.8% |
| | 21 | * | Rye | 0.43 | 0.13 | −0.30 | −70.1% |
| | Mean | | | 0.66 | 0.44 | −0.22 | −33.7% |
| Placebo Treatment Group | 1 | * | Grass pollen | 0.37 | 1.03 | 0.66 | 180.3% |
| | 2 | | House dust mite | 0.33 | 0.22 | −0.10 | −31.7% |
| | 3 | * | Cat | 0.47 | 0.28 | −0.19 | −41.0% |
| | 4 | * | Birch pollen | 0.47 | 0.94 | 0.47 | 99.4% |
| | 5 | | Rye | 0.39 | 0.13 | −0.26 | −67.4% |
| | 6 | | Grass pollen | 0.49 | 0.72 | 0.23 | 47.0% |
| | 7 | * | Cat | 0.25 | 0.28 | 0.03 | 13.9% |
| | 8 | * | Rye | 1.14 | 0.98 | −0.16 | −13.8% |
| | 9 | * | Horse hair | 0.24 | −0.02 | −0.26 | −108.0% |
| | 10 | | Grass pollen | 0.53 | 0.30 | −0.23 | −43.0% |
| | 11 | * | House dust mite | 0.35 | 0.41 | 0.07 | 19.4% |
| | 12 | | Grass pollen | 0.31 | 0.06 | −0.25 | −80.9% |
| | 13 | | Grass pollen | 1.17 | 1.64 | 0.47 | 40.7% |
| | 14 | * | House dust mite | 1.27 | 1.00 | 0.35 | 27.0% |
| | 15 | * | House dust mite | 0.96 | 0.93 | −0.03 | −2.7% |
| | 16 | * | Grass pollen | 1.29 | 1.29 | −0.01 | −0.4% |
| | 17 | | Rye | 0.54 | 0.33 | −0.21 | −39.0% |
| | 18 | * | Birch pollen | 0.11 | −0.34 | −0.45 | −411.9% |
| | Mean | | | 0.59 | 0.60 | 0.01 | 1.4% |

* Patient included in pre-specified subgroup with blood eosinophils ≥4%.

SUPPLEMENTARY APPENDIX TABLE S4B

Individual early-phase asthmatic response (EAR, 0-3 h) to allergen challenge

|  |  |  |  | AUC (h) | | | |
|---|---|---|---|---|---|---|---|
| Patient | | Blood Eos | Allergen Used | Pre-Treatment | Post-Treatment | Absolute Change | % Change |
| SB010 Treatment Group | 1 | * | Birch pollen | 0.16 | 0.21 | 0.04 | 26.2% |
| | 2 | | Birch pollen | 0.54 | 0.29 | −0.26 | −47.3% |
| | 3 | * | Cat | 0.87 | 0.32 | −0.55 | −63.6% |
| | 4 | | Grass pollen | 0.24 | 0.23 | −0.01 | −5.4% |
| | 5 | * | House dust mite | 0.22 | 0.20 | −0.02 | −9.2% |
| | 6 | * | Dog | 0.14 | −0.07 | −0.21 | −146.5% |
| | 7 | * | Cat | −0.08 | 0.04 | 0.12 | −157.3% |
| | 8 | * | Birch pollen | 0.48 | 0.00 | −0.48 | −99.6% |
| | 9 | | Grass mix | 0.63 | 0.49 | −0.14 | −21.8% |
| | 10 | | House dust mite | 0.28 | 0.21 | −0.07 | −23.5% |
| | 11 | * | Grass pollen | −0.03 | 0.10 | 0.12 | −473.1% |
| | 12 | | House dust mite | 0.35 | 0.53 | 0.19 | 53.5% |
| | 13 | | House dust mite | 0.74 | 0.88 | 0.14 | 18.2% |
| | 14 | * | House dust mite | −0.01 | 0.33 | 0.33 | −5516.7% |
| | 15 | | Birch pollen | 0.81 | 0.95 | 0.14 | 17.2% |
| | 16 | | Birch pollen | 0.45 | 0.82 | 0.37 | 84.0% |
| | 17 | * | Cat | 0.34 | 0.17 | −0.16 | −49.0% |
| | 18 | * | Birch pollen | 0.47 | 0.39 | −0.08 | −17.6% |
| | 19 | | Dog | 0.74 | 0.38 | −0.36 | −48.9% |
| | 20 | * | Rye | 0.30 | 0.06 | −0.24 | −80.1% |
| | 21 | * | Rye | 0.31 | 0.54 | 0.24 | 76.6% |
| | Mean | | | 0.38 | 0.34 | −0.04 | −11.3% |
| Placebo Treatment Group | 1 | * | Grass pollen | 0.01 | 0.75 | 0.74 | 8266.7% |
| | 2 | | House dust mite | 0.31 | 0.24 | −0.07 | −22.7% |
| | 3 | * | Cat | 0.40 | 0.35 | −0.06 | −11.7% |
| | 4 | * | Birch pollen | 0.47 | 0.03 | 0.10 | 34.10% |
| | 5 | | Rye | 0.52 | 0.33 | −0.19 | −36.9% |
| | 6 | | Grass pollen | 0.59 | 0.83 | 0.25 | 41.7% |
| | 7 | * | Cat | 0.23 | 0.39 | 0.16 | 68.7% |
| | 8 | * | Rye | 0.41 | 0.23 | −0.19 | −45.0% |
| | 9 | * | Horse hair | 0.22 | 0.22 | 0.00 | −0.5% |
| | 10 | | Grass pollen | 0.39 | 0.40 | 0.01 | 3.1% |
| | 11 | * | House dust mite | 0.58 | 0.51 | −0.08 | −12.9% |

SUPPLEMENTARY APPENDIX TABLE S4B-continued

Individual early-phase asthmatic response (EAR, 0-3 h) to allergen challenge

| Patient | Blood Eos | Allergen Used | AUC (h) Pre-Treatment | Post-Treatment | Absolute Change | % Change |
|---|---|---|---|---|---|---|
| 12 |   | Grass pollen | 0.66 | 0.34 | −0.32 | −48.3% |
| 13 |   | Grass pollen | 0.88 | 1.06 | 0.19 | 21.5% |
| 14 | * | House dust mite | 0.32 | 0.72 | 0.40 | 125.8% |
| 15 | * | House dust mite | 0.62 | 0.64 | 0.02 | 3.2% |
| 16 | * | Grass pollen | 0.71 | 0.61 | −0.11 | −14.9% |
| 17 |   | Rye | 0.20 | 0.40 | 0.20 | 96.1% |
| 18 | * | Birch pollen | 0.11 | −0.23 | −0.33 | −318.1% |
| 19 | * | Rye | 0.18 | 0.21 | 0.04 | 21.0% |
| Mean |   |   | 0.41 | 0.45 | 0.04 | 10.5% |

* Patient included in pre-specified subgroup with blood eosinophils ≥4%.

SUPPLEMENTARY APPENDIX TABLE S5

Effect of 28 days SB010 or placebo treatment on post-challenge FeNO and PC20 levels

|   | Pre Median | Pre IQR | Post Median | Post IQR | P value |
|---|---|---|---|---|---|
| FeNO (ppb) |   |   |   |   |   |
| SB010 | 85.33 | 47.67 | 68.00 | 36.33 | 0.37 |
| Placebo | 65.00 | 44.58 | 74.50 | 45.33 |   |
| PC20 (mg/dl) |   |   |   |   |   |
| SB010 | 0.30 | 1.33 | 0.44 | 0.94 | 0.54 |
| Placebo | 0.49 | 0.69 | 0.37 | 0.71 |   |

Legend Table S5: Effect of 28 Days SB010 or Placebo Treatment on Post-Challenge FeNO and PC20 Levels Effect of 28 days SB010 or placebo treatment on FeNO and PC20 levels. Measurements of FeNO levels and assessment of airway hyper-responsiveness (PC20) were performed following the allergen-challenges before and after the 28 days course of SB010 or placebo treatment. FeNO levels are expressed as ppb, PC20 is expressed in methacholine mg/dl. P values were calculated by Wilcoxon rank sum text.

SUPPLEMENTARY APPENDIX TABLE S6

Effect of 28 days SB010 or placebo treatment on non-challenged FeNO levels

|   | Pre treatment Median | IQR | 60 days follow-up Median | IQR | P value |
|---|---|---|---|---|---|
| all |   |   |   |   |   |
| SB010 | 46.67 | 30.67 | 38.67 | 35.17 | 0.14 |
| Placebo | 41.67 | 32.25 | 38.42 | 48.50 |   |
| EOS ≥ 4% |   |   |   |   |   |
| SB010 | 63.83 | 32.75 | 37.50 | 34.83 | 0.15 |
| Placebo | 46.33 | 22.00 | 62.50 | 45.17 |   |
| FeNO ≥ 40 ppb |   |   |   |   |   |
| SB010 | 63.83 | 21.00 | 43.67 | 30.17 | 0.15 |
| Placebo | 46.33 | 21.33 | 62.50 | 37.00 |   |

Legend Table S6: Effect of 28 Days SB010 or Placebo Treatment on Non-Challenged FeNO Levels FeNO was measured at baseline pre-allergen challenge and pre-treatment followed by measurements on day 88 at the end of the 60 days follow-up period. Shown are median and inter-quartile ranges (IQR) for the intention-to-treat study population, as well as for the prespecified subgroups of blood Eos ≥4% and baseline FeNO ≥40 ppb. P-values were calculated by Wilcoxon rank sum test.

SUPPLEMENTARY APPENDIX TABLE S7

| Safety Biomarkers | | | | | | | | | |
|---|---|---|---|---|---|---|---|---|---|
|   | SB010 Treatment Group | | | | Placebo Treatment Group | | | | |
|   | Pre-Treatment | | Post-Treatment | | Pre-Treatment | | Post-Treatment | | |
|   | Median | IQR | Median | IQR | Median | IQR | Median | IQR | p Value |
| In Sputum |   |   |   |   |   |   |   |   |   |
| TNFa | 5.18 | 4.19 | 7.43 | 8.51 |   |   |   |   |   |
| IL-1b | 16.44 | 34.27 | 28.79 | 51.90 |   |   |   |   |   |
| IL-8 | 855.95 | 934.34 | 948.05 | 1,436.10 |   |   |   |   |   |
| In Plasma |   |   |   |   |   |   |   |   |   |
| TNFa | 2.84 | 3.04 | 2.76 | 2.86 | 2.69 | 3.85 | 2.87 | 3.44 | 0.95 |
| IL-8 | 6.17 | 2.37 | 6.18 | 3.06 | 5.77 | 1.85 | 6.20 | 2.81 | 0.24 |
| MCP-1 | 228.83 | 42.73 | 219.23 | 53.93 | 244.22 | 59.72 | 238.87 | 65.16 | 0.74 |
| MCP-4 | 334.49 | 162.81 | 348.54 | 174.88 | 366.60 | 229.67 | 312.84 | 233.00 | 0.69 |

SUPPLEMENTARY APPENDIX TABLE S7-continued

Safety Biomarkers

| | SB010 Treatment Group | | | | Placebo Treatment Group | | | | |
|---|---|---|---|---|---|---|---|---|---|
| | Pre-Treatment | | Post-Treatment | | Pre-Treatment | | Post-Treatment | | |
| | Median | IQR | Median | IQR | Median | IQR | Median | IQR | p Value |
| MIP-1b | 74.94 | 20.71 | 82.01 | 29.85 | 88.34 | 28.47 | 82.33 | 23.23 | 0.30 |
| MDC | 4,202.15 | 1,957.44 | 3,876.35 | 2,222.62 | 3,238.25 | 1,493.30 | 3,653.38 | 1,223.84 | 0.69 |
| IP-10 | 180.82 | 50.98 | 165.88 | 52.24 | 194.44 | 156.78 | 197.88 | 164.14 | 0.72 |

Blood IL-4, IL-13 and IFN-γ: Most values below lower limit of quantification; IL-5 see Supplementary Appendix FIG. S6.

SUPPLEMENTARY APPENDIX TABLE S8

Differential cell count in sputum - expressed as cells ×10$^6$/g sputum)

| | | Eosinophils | | Neutrophils | | Lymphocytes | | Monocytes | |
|---|---|---|---|---|---|---|---|---|---|
| | | Mean | STD | Mean | STD | Mean | STD | Mean | STD |
| SB010 | Pre Treatment | 1.9 | 2.8 | 5.1 | 11.7 | 0.1 | 0.4 | 0.3 | 0.9 |
| | Post Treatment | 0.9 | 1.3 | 1.8 | 2.6 | 0.0 | 0.0 | 0.1 | 0.1 |
| Placebo | Pre Treatment | 0.8 | 1.0 | 3.3 | 5.3 | 0.1 | 0.2 | 0.1 | 0.1 |
| | Post Treatment | 1.7 | 4.2 | 4.2 | 8.9 | 0.0 | 0.1 | 0.1 | 0.1 |

Table shows mean values plus standard deviation/post allergen changes pre and post treatment, respectively.

SUPPLEMENTARY APPENDIX TABLE S9

List of study endpoints

| Endpoint | Measurement time-points | Data |
|---|---|---|
| Primary Endpoint | | |
| Late Phase Asthmatic Response (LAR), AUC | Day −54 to −16, −1, 28 | Data included in manuscript |
| Secondary Endpoint | | |
| Safety and Tolerability | Throughout study | Adverse events and immune monitoring included in manuscript |
| Exploratory Endpoints | | |
| LAR, maximum decline | Day −54 to −15, −1, 28 | Data included in manuscript |
| Early Phase Asthmatic Response (EAR) AUC and maximum decline | Day −54 to −15, −1, 28 | Data included in manuscript |
| PC$_{20}$ | Day −56 to −17, 0, 29 | Data included in manuscript appendix |
| FeNO | Day −1, 0, 1, 13, 28, 29, 88 | Data included in manuscript appendix |
| Sputum analysis | Day −56 to −17, −53 to −14, 0, 26, 29 | Differential cell count (% eosinophils) included in manuscript; cytokine and mRNA measurements not meaningful due to low sputum volume; all measureable cytokines included in Table S6; tryptase included in manuscript |
| Systemic biomarkers | Day −1, 0, 28, 29 | IL-5 included in manuscript; no SB010-specific effect apparent in other biomarkers |
| Subgroup analyses (LAR AUC and maximum decline; EAR AUC and maximum decline) | Day −54 to −15, −1, 28 | Key subgroups included in manuscript |
| Pharmacokinetics | Day 1, 28/29 | Data not included in manuscript |

REFERENCE LIST

1. Global Strategy for Asthma Management and Prevention. From the Global Strategy for Asthma Management and Prevention, Global Initiative for Asthma (GINA) 2014. www.ginathma.org; http://www.ginasthma.org/local/uploads/files/GINA_Report_2014.pdf 2. Bhakta N R, Woodruff P G. Human asthma phenotypes: from the clinic, to cytokines, and back again. Immunol Rev 2011; 242(1):220-232.

3. Woodruff P G, Modrek B, Choy D F et al. T-helper type 2-driven inflammation defines major subphenotypes of asthma. Am J Respir Crit Care Med 2009; 180(5):388-395.

4. Holgate S T. Innate and adaptive immune responses in asthma. Nat Med 2012; 18(5):673-683.
5. Wenzel S E. Asthma phenotypes: the evolution from clinical to molecular approaches. Nat Med 2012; 18(5):716-725.
6. Ray A, Cohn L. Th2 cells and GATA-3 in asthma: new insights into the regulation of airway inflammation. J Clin Invest 1999; 104(8):985-993.
7. Bergqvist A, Andersson C K, Hoffmann H J et al. Marked epithelial cell pathology and leukocyte paucity in persistently symptomatic severe asthma. Am J Respir Crit Care Med 2013; 188(12):1475-1477.
8. Holgate S T. Trials and tribulations in identifying new biologic treatments for asthma. Trends Immunol 2012; 33(5):238-246.
9. Cho E A, Moloney F J, Cai H et al. Safety and tolerability of an intratumorally injected DNAzyme, Dz13, in patients with nodular basal-cell carcinoma: a phase first-in-human trial (DISCOVER). Lancet 2013; 381(9880):1835-1843.
10. Santiago F S, Khachigian L M. Nucleic acid based strategies as potential therapeutic tools: mechanistic considerations and implications to restenosis. J Mol Med (Berl) 2001; 79(12):695-706.
11. Sel S, Wegmann M, Dicke T et al. Effective prevention and therapy of experimental allergic asthma using a GATA-3-specific DNAzyme. J Allergy Clin Immunol 2008; 121(4):910-916.
12. Turowska A, Librizzi D, Baumgartl N et al. Biodistribution of the GATA-3-specific DNAzyme hgd40 after inhalative exposure in mice, rats and dogs. Toxicol Appl Pharmacol 2013; 272(2):365-372.
13. Dicke T, Pali-Scholl I, Kaufmann A, Bauer S, Renz H, Garn H. Absence of unspecific innate immune cell activation by GATA-3-specific DNAzymes. Nucleic Acid Ther 2012; 22(2):117-126.
14. Fuhst R, Runge F, Buschmann J et al. Toxicity profile of the GATA-3-specific DNAzyme hgd40 after inhalation exposure. Pulm Pharmacol Ther 2013; 26(2):281-289.
15. Global Initiative for Asthma (GINA): Global strategy for asthma management and prevention. 2008. www.ginasthma.org. Eur Respir J 2008; 31: 143-178.
16. Brand P, Beckmann H, Maas E M et al. Peripheral deposition of alpha1-protease inhibitor using commercial inhalation devices. Eur Respir J 2003; 22(2):263-267.
17. Cockcroft D W, Murdock K Y, Kirby J, Hargreave F. Prediction of airway responsiveness to allergen from skin sensitivity to allergen and airway responsiveness to histamine. Am Rev Respir Dis 1987; 135(1):264-267.
18. Diamant Z, Gauvreau G M, Cockcroft D W et al. Inhaled allergen bronchoprovocation tests. J Allergy Clin Immunol 2013; 132(5):1045-1055.
19. Gauvreau G M, Watson R M, Rerecich T J, Baswick E, Inman M D, O'Byrne P M. Repeatability of allergen-induced airway inflammation. J Allergy Clin Immunol 1999; 104(1):66-71.
20. Miller M R, Hankinson J, Brusasco V et al. Standardisation of spirometry. Eur Respir J 2005; 26(2):319-338.
21. Crapo R O, Casaburi R, Coates A L et al. Guidelines for methacholine and exercise challenge testing-1999. This official statement of the American Thoracic Society was adopted by the ATS Board of Directors, July 1999. Am J Respir Crit Care Med 2000; 161(1):309-329.
22. ATS/ERS recommendations for standardized procedures for the online and offline measurement of exhaled lower respiratory nitric oxide and nasal nitric oxide, 2005. Am J Respir Crit Care Med 2005; 171(8):912-930.
23. Janssen O, Schaumann F, Holz O et al. Low-dose endotoxin inhalation in healthy volunteers—a challenge model for early clinical drug development. BMC Pulm Med 2013; 13:19.
24. O'Byrne P M. Allergen-induced airway inflammation and its therapeutic intervention. Allergy Asthma Immunol Res 2009; 1(1):3-9.
25. Wenzel S, Wilbraham D, Fuller R, Getz E B, Longphre M. Effect of an interleukin-4 variant on late phase asthmatic response to allergen challenge in asthmatic patients: results of two phase 2a studies. Lancet 2007; 370(9596):1422-1431.
26. Wenzel S, Ford L, Pearlman D et al. Dupilumab in persistent asthma with elevated eosinophil levels. N Engl J Med 2013; 368(26):2455-2466.
27. Corren J, Busse W, Meltzer E O et al. A randomized, controlled, phase 2 study of AMG 317, an IL-4Ralpha antagonist, in patients with asthma. Am J Respir Crit Care Med 2010; 181(8):788-796.
28. Haldar P, Brightling C E, Hargadon B et al. Mepolizumab and exacerbations of refractory eosinophilic asthma. N Engl J Med 2009; 360(10):973-984.
29. Nair P, Pizzichini M M, Kjarsgaard M et al. Mepolizumab for prednisone113 dependent asthma with sputum eosinophilia. N Engl J Med 2009; 360(10):985-993.
30. Pavord I D, Korn S, Howarth P et al. Mepolizumab for severe eosinophilic asthma (DREAM): a multicentre, double-blind, placebo-controlled trial. Lancet 2012; 380 (9842):651-659.
31. Corren J, Lemanske R F, Hanania N A et al. Lebrikizumab treatment in adults with asthma. N Engl J Med 2011; 365(12):1088-1098.
32. Ingram J L, Kraft M. IL-13 in asthma and allergic disease: asthma phenotypes and targeted therapies. J Allergy Clin Immunol 2012; 130(4):829-842.
33. Gauvreau G M, O'Byrne P M, Boulet L P et al. Effects of an Anti-TSLP Antibody on Allergen-Induced Asthmatic Responses. N Engl J Med 2014.
34. Petsky H L, Cates C J, Lasserson T J et al. A systematic review and meta-analysis: tailoring asthma treatment on eosinophilic markers (exhaled nitric oxide or sputum eosinophils). Thorax 2012; 67(3)199-208.
35. Vijverberg S J, Hilvering B, Raaijmakers J A, Lammers J W, Maitland-van der Zee A H, Koenderman L. Clinical utility of asthma biomarkers: from bench to bedside. Biologics 2013; 7:199-210.
36. Wenzel S. Severe asthma: from characteristics to phenotypes to endotypes. Clin Exp Allergy 2012; 42(5):650-658.
37. Brusselle G G, Maes T, Bracke K R. Eosinophils in the spotlight: Eosinophilic airway inflammation in nonallergic asthma. Nat Med 2013; 19(8):977-979.
38. Fahy J V, Fleming H E, Wong H H et al. The effect of an anti-IgE monoclonal antibody on the early- and late-phase responses to allergen inhalation in asthmatic subjects. Am J Respir Crit Care Med 1997; 155(6):1828-1834.
39. Winandy S, Brown M. No DL1 Notch ligand? GATA be a mast-cell. Nat Immunol 2007; 8(8):796-798.
40. Mjosberg J, Bernink J, Golebski K et al. The transcription factor GATA3 is essential for the function of human type 2 innate lymphoid cells. Immunity 2012; 37(4):649-659.
41. Sadat M A, Kumatori A, Suzuki S, Yamaguchi Y, Tsuji Y, Nakamura M. GATA-3 represses gp91phox gene expression in eosinophil-committed HL-60-C15 cells. FEBS Lett 1998; 436(3):390-394.

42. Gauvreau G M, Boulet L P, Postma D S et al. Effect of low-dose ciclesonide on allergen-induced responses in subjects with mild allergic asthma. J Allergy Clin Immunol 2005; 116(2):285-291.
43. Kent S E, Boyce M, Diamant Z et al. The 5-lipoxygenase-activating protein inhibitor, GSK2190915, attenuates the early and late responses to inhaled allergen in mild asthma. Clin Exp Allergy 2013; 43(2)177-186.

The invention claimed is:

1. A method of treatment of a patient suffering from Th2-driven asthma, wherein the patient is characterized by (i) a blood eosinophil count of 3% or more; and/or (ii) blood eosinophil count of $350 \times 10^6$/L or more; and/or (iii) fractional expiratory nitric oxide of 40 ppb or more comprising administering to said patient an effective amount of a nucleic acid-based inactivator of GATA-3.

2. The method according to claim 1, wherein said nucleic acid-based inactivator is a DNAzyme directed at GATA-3.

3. The method according to claim 1, wherein said patient has a blood eosinophil count of 4% or more.

4. The method according to claim 1, wherein said patient has a blood eosinophil count of $350 \times 10^6$/L or more.

5. The method according to claim 3, wherein said blood eosinophil count is determined by (i) automated differential blood counting; or (ii) by manual microscopic cell differentiation using conventional blood smears.

6. The method according to claim 1, wherein said patient has fractional expiratory nitric oxide of 40 ppb or more.

7. The method according to claim 6, wherein said fractional expiratory nitric oxide is determined using a hand-held device.

8. The method according to claim 1, wherein said nucleic acid-based inactivator of GATA-3 is the DNAzyme hgd40 (SEQ ID NO: 3).

9. The method according to claim 8, wherein said hgd40 is comprised in a formulation for inhalation.

10. The method according to claim 9, wherein said hgd40 is dissolved in PBS.

11. The method according to claim 10, wherein between 5 and 50 mg of hgd40 are dissolved in 2 ml PBS.

12. The method according to claim 1, wherein said nucleic acid-based inactivator of GATA-3 is administered once daily, two times daily or three times daily, particularly once daily.

13. The method according to claim 12, wherein said nucleic acid-based inactivator of GATA-3 is administered once daily in continuous therapy, in particular maintenance therapy.

14. The method according to claim 1, wherein said nucleic acid-based inactivator is used as add-on therapy to one or more inhaled or oral therapeutics for the treatment of asthma selected from the list of: corticosteroids, long-acting beta agonists (LABAs), long acting muscarinic antagonists (LAMAs), antileukotrienes, short-acting beta agonists (SABAs), anticholinergics and monoclonal antibodies.

15. The method according to claim 1 wherein the patient is characterized by (i) a blood eosinophil count of 4% or more.

16. The method according to claim 1 wherein the patient is characterized by (i) a blood eosinophil count of 5% or more.

17. The method according to claim 1 wherein the patient is characterized by (ii) blood eosinophil count of $450 \times 10^6$/L or more.

18. The method according to claim 10, wherein between 5 and 20 mg of hgd40 are dissolved in 2 ml PBS.

19. The method according to claim 10, wherein 10 mg of hgd40 is dissolved in 2 ml PBS.

\* \* \* \* \*

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Synthetic Polypeptide

<400> SEQUENCE: 1
ggctagctac aacga                                                    15

<210> SEQ ID NO 2
<211> LENGTH: 33
<212> TYPE: DNA
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(9)
<223> OTHER INFORMATION: n is a, c, g, t or u
<220> FEATURE:
<221> NAME/KEY: misc_feature
<222> LOCATION: (25)..(33)
<223> OTHER INFORMATION: n is a, c, g, t or u

<400> SEQUENCE: 2
nnnnnnnnng gctagctaca acgannnnnn nnn                                33

<210> SEQ ID NO 3
<211> LENGTH: 33
<212> TYPE: DNA
<213> ORGANISM: Artificial Sequence
<220> FEATURE:
<223> OTHER INFORMATION: Synthetic Polypeptide

<400> SEQUENCE: 3
gtggatggag gctagctaca acgagtcttg gag                                33
```